United States Patent
Weng et al.

(10) Patent No.: US 8,481,688 B2
(45) Date of Patent: Jul. 9, 2013

(54) ANTI-FGFR2 ANTIBODIES

(75) Inventors: Zhigang Weng, Brookline, MA (US); William M. Winston, Jr., Marlborough, MA (US); Ailin Bai, Newton, MA (US); Kristan Meetze, Lexington, MA (US); Solly Weiler, Newton, MA (US); Ting Chen, Acton, MA (US); Jeno Gyuris, Lincoln, MA (US)

(73) Assignee: AVEO Pharmaceuticals, Inc., Cambridge, MA (US)

( * ) Notice: Subject to any disclaimer, the term of this patent is extended or adjusted under 35 U.S.C. 154(b) by 86 days.

(21) Appl. No.: 13/105,521

(22) Filed: May 11, 2011

(65) Prior Publication Data

US 2011/0305687 A1 Dec. 15, 2011

Related U.S. Application Data

(60) Provisional application No. 61/333,590, filed on May 11, 2010.

(51) Int. Cl.
*C07K 16/28* (2006.01)

(52) U.S. Cl.
USPC ............... 530/388.22; 530/350; 530/387.1; 530/387.3; 530/387.7

(58) Field of Classification Search
USPC ............ 530/350, 387.1, 387.3, 387.7, 388.22
See application file for complete search history.

(56) References Cited

U.S. PATENT DOCUMENTS

| | | | |
|---|---|---|---|
| 5,707,632 A | 1/1998 | Williams et al. | |
| 5,863,888 A | 1/1999 | Dionne et al. | |
| 6,344,546 B1 | 2/2002 | Dionne et al. | |
| 6,384,191 B1 | 5/2002 | Williams et al. | |
| 7,429,645 B2 | 9/2008 | Garber et al. | |
| 8,101,721 B2 | 1/2012 | Yayon et al. | |
| 8,101,723 B2 | 1/2012 | Kim et al. | |
| 2003/0228605 A1 | 12/2003 | Slootstra et al. | |
| 2004/0116330 A1 | 6/2004 | Naito et al. | |
| 2005/0003465 A1 | 1/2005 | Reiter et al. | |
| 2005/0037001 A1 | 2/2005 | Germeraad et al. | |
| 2005/0249728 A1 | 11/2005 | Singh et al. | |
| 2006/0263369 A1 | 11/2006 | Bicknell et al. | |
| 2007/0071675 A1 | 3/2007 | Wu et al. | |
| 2007/0248605 A1 | 10/2007 | Hestir et al. | |
| 2008/0025980 A1 | 1/2008 | Hardy et al. | |
| 2008/0219974 A1 | 9/2008 | Bernett et al. | |
| 2009/0012268 A1 | 1/2009 | Bergmann et al. | |
| 2009/0117115 A1 | 5/2009 | Paul et al. | |
| 2009/0311250 A1 | 12/2009 | Chant et al. | |
| 2010/0068199 A1 | 3/2010 | Liang et al. | |
| 2010/0092457 A1 | 4/2010 | Aburatani et al. | |
| 2010/0098692 A1 | 4/2010 | Theuer et al. | |
| 2010/0104553 A1 | 4/2010 | Frey et al. | |
| 2010/0111944 A1 | 5/2010 | Pollock et al. | |
| 2011/0059091 A1 | 3/2011 | Chang et al. | |
| 2012/0059047 A1 | 3/2012 | Prins et al. | |

FOREIGN PATENT DOCUMENTS

| | | |
|---|---|---|
| WO | WO-01/81581 | 11/2001 |
| WO | WO-2007/124463 | 11/2007 |
| WO | WO-2008/020596 | 2/2008 |
| WO | WO-2009/072604 | 6/2009 |
| WO | WO-2010/040083 A3 | 4/2010 |
| WO | WO-2011/025814 A1 | 3/2011 |
| WO | WO-2012/021841 A3 | 2/2012 |

OTHER PUBLICATIONS

Adnane et al. (1991) "BEK and FLG, two receptors to members of the FGF family, are amplified in subsets of human breast cancers" Oncogene 6:659-663.
Bai et al. (2010) "GP369, an FGFR2-IIIb-specific antibody, exhibits potent antitumor activity against human cancers driven by activated FGFR2 signaling" Cancer Res. 70:7630-7639.
Beenken et al. (2009) "The FGF family: biology, pathophysiology and therapy" Nature Reviews Drug Discovery 8:235-254.
Chang et al. (2005) "Immunohistochemistry accurately predicts FGFR3 aberrant expression and t(4;14) in multiple myeloma" Blood 106:353-355.
Davies et al. (2005) "Somatic Mutations of the Protein Kinase Gene Family in Human Lung Cancer" Cancer Res. 65:7591-7595.
Ding et al. (2008) "Somatic mutations affect key pathways in lung adenocarcinoma" Nature 455:1069-1075.
Dutt et al. (2008) "Drug-sensitive FGFR2 mutations in endometrial carcinoma" Proc. Natl. Acad. Sci. USA 105:8713-8717.
Easton et al. (2007) "Genome-wide association study identifies novel breast cancer susceptibility loci" Nature 447:1087-1093.
Eswarakumar et al. (2005) "Cellular signaling by fibroblast growth factor receptors" Cytokine Growth Factor Rev. 16:139-149.
Gomez-Roman et al. (2005) "Fibroblast Growth Factor Receptor 3 Is Overexpressed in Urinary Tract Carcinomas and Modulates the Neoplastic Cell Growth" Clin. Cancer Res. 11:459-65.
Greenman et al. (2007) "Patterns of somatic mutation in human cancer genomes" Nature 446:153-158.
Hara et al. (1998) "Amplification of c-myc, K-sam, and c-met in gastric cancers: detection by fluorescence in situ hybridization" Lab. Invest. 78:1143-1153.
Hunter et al. (2007) "A genome-wide association study identifies alleles in FGFR2 associated with risk of sporadic postmenopausal breast cancer" Nat. Genet. 39:870-874.
Written Opinion, International Patent Application No. PCT/US2011/036085, mailed on Nov. 14, 2011 (10 pages).
Jang et al. (2001) "Mutations in Fibroblast Growth Factor Receptor 2 and Fibroblast Growth Factor Receptor 3 Genes Associated with Human Gastric and Colorectal Cancers" Cancer Res. 61:3541-3543.
Katoh (2008) "Cancer genomics and genetics of *FGFR2* (Review)" International Journal of Oncology 33:233-237.
Katoh (2009) "FGFR2 Abnormalities Underlie a Spectrum of Bone, Skin, and Cancer Pathologies" Journal of Investigative Dermatology 129:1861-1867.
Katoh et al. (2009) "FGFR2-related pathogenesis and FGFR2-targeted therapeutics (Review)" International Journal of Molecular Medicine 23:307-311.
Larocca et al. (1998) "Establishment of Epitope-Defined Monoclonal Antibodies With Specificity for Fibroblast Growth Factor Receptor Types 1 and 2" Hybridoma 17:21-31.

(Continued)

*Primary Examiner* — Stephen Rawlings
(74) *Attorney, Agent, or Firm* — Goodwin Procter LLP

(57) ABSTRACT

Monoclonal antibodies that bind and inhibit biological activities of human FGFR2 are disclosed. The antibodies can be used to treat cell proliferative diseases and disorders, including certain forms of cancer, associated with activation or overexpression of FGFR2.

7 Claims, 12 Drawing Sheets

OTHER PUBLICATIONS

Meyer et al. (2008) "Allele-Specific Up-Regulation of FGFR2 Increases Susceptibility to Breast Cancer" Plos Biol. 6(e108):1098-1103.

Mor et al. (1993) "DNA amplification in human gastric carcinomas" Cancer Genet. Cytogenet. 65:111-114.

Pollock et al. (2007) "Frequent activating FGFR2 mutations in endometrial carcinomas parallel germline mutations associated with craniosynostosis and skeletal dysplasia syndromes" Oncogene 26:7158-7162.

Turner et al. (2010) "Fibroblast growth factor signalling: from development to cancer" Nature Reviews Cancer 10:116-129.

Turner et al. (2010) "Integrative molecular profiling of triple negative breast cancers identifies amplicon drivers and potential therapeutic targets" Oncogene 29:2013-2023.

Venkateswaran et al. (1992) "Production of anti-fibroblast growth factor receptor monoclonal antibodies by in vitro immunization" Hybridoma 11:729-39.

Wei et al. (2006) "Generation and Characterization of Monoclonal Antibodies to Human Keratinocyte Growth Factor Receptor" Hybridoma 25:115-124.

Complete Heavy Chain Variable Region Amino Acid Alignments

```
Antibody                         CDR1                                        CDR2
   4B9 Heavy        EVQLQQSGTVLARPGASVKMSCKTSGYTFT[SYWMH]WVKQRPGQGLEWIG[AIYPGNSDTDYSQKFKG]KATL
   Hu4B9-65 Heavy   QVQLVQSGAEVKKPGSSVKVSCKASGYTFT[SYWMH]WVRQAPGQGLEWMG[AIYPGNSDTDYSQKFKG]RVTI
   Hu4B9-82, -83 Heavy QVQLVQSGAEVKKPGSSVKVSCKASGYTFS[SYWMH]WVRQAPGQGLEWMG[AIYPGNSDTDYSQKFQG]RVTI CDR3
   4B9 Heavy        TAVTSATTAYMELSSLTNEDSAVYYCSK[FDY]WGQGTTLTVSS  (SEQ ID NO: 2)
   Hu4B9-65 Heavy   TADESTSTAYMELSSLRSEDTAVYYCSK[FDY]WGQGTLVTVSS  (SEQ ID NO: 35)
   Hu4B9-82, -83 Heavy TADESTSTAYMELSSLRSEDTAVYYCSK[FDY]WGQGTLVTVSS  (SEQ ID NO: 37)
```

FIG. 8

Heavy Chain CDR Amino Acid Alignments

| Antibody | CDR1 | CDR2 | CDR3 |
|---|---|---|---|
| 4B9 Heavy | SYWMH (SEQ ID NO: 5) | AIYPGNSDTDYSQKFKG (SEQ ID NO: 6) | FDY |
| Hu4B9-65 Heavy | SYWMH (SEQ ID NO: 5) | AIYPGNSDTDYSQKFKG (SEQ ID NO: 6) | FDY |
| Hu4B9-82, -83 Heavy | SYWMH (SEQ ID NO: 5) | AIYPGNSDTDYSQKFQG (SEQ ID NO: 38) | FDY |

FIG. 9

Complete Light (Kappa) Chain Variable Region Amino Acid Alignments

| Antibody | | CDR1 | | CDR2 |
|---|---|---|---|---|
| 4B9 Kappa | QIVLTQSPALMSASPGEKVTMTC | SASSSVNYMY | WYQQKPRSSPKPWIY | LTSNLAS | GVPARFSGRGSGTSY |
| Hu4B9-65 Kappa | EIVLTQSPATLSLSPGERATLSC | RASSSVNYMY | WYQQKPGQAPRPWIY | LTSNRAT | GVPARFSGSGSGTDY |
| Hu4B9-82 Kappa | EIVLTQSPATLSLSPGERATLSC | RASSSVNYMY | WYQQKPGQAPRPWIY | LTSNRAT | GIPARFSGSGSGTDY |
| Hu4B9-83 Kappa | EIVLTQSPATLSLSPGERATLSC | RASSSVNYMY | WYQQKPGQAPRPWIY | LTSNRAT | GIPARFSGSGSGTDF |

| | | CDR3 | | |
|---|---|---|---|---|
| 4B9 Kappa | SLTISSMEAEDAATYYC | QQWSSNPYT | FGGGTKLEIK | (SEQ ID NO: 4) |
| Hu4B9-65 Kappa | TLTISSLEPEDFAVYYC | QQWSSNPYT | FGQGTKLEIK | (SEQ ID NO: 40) |
| Hu4B9-82 Kappa | TLTISSLEPEDFAVYYC | QQWSSNPYT | FGQGTKLEIK | (SEQ ID NO: 44) |
| Hu4B9-83 Kappa | TLTISSLEPEDFAVYYC | QQWSSNPYT | FGQGTKLEIK | (SEQ ID NO: 46) |

FIG. 10

Light (Kappa) Chain CDR Amino Acid Alignments

| Antibody | CDR1 | | CDR2 | | CDR3 | |
|---|---|---|---|---|---|---|
| 4B9 Kappa | SASSSVNYMY | (SEQ ID NO: 12) | LTSNLAS | (SEQ ID NO: 13) | QQWSSNPYT | (SEQ ID NO: 14) |
| Hu4B9-65 Kappa | RASSSVNYMY | (SEQ ID NO: 41) | LTSNRAT | (SEQ ID NO: 42) | QQWSSNPYT | (SEQ ID NO: 14) |
| Hu4B9-82 Kappa | RASSSVNYMY | (SEQ ID NO: 41) | LTSNRAT | (SEQ ID NO: 42) | QQWSSNPYT | (SEQ ID NO: 14) |
| Hu4B9-83 Kappa | RASSSVNYMY | (SEQ ID NO: 41) | LTSNRAT | (SEQ ID NO: 42) | QQWSSNPYT | (SEQ ID NO: 14) |

FIG. 11

SEQUENCE LISTING

<160> NUMBER OF SEQ ID NOS: 62

<210> SEQ ID NO 1
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gaggttcagc tccagcagtc tgggactgtg ctggcaaggc ctggggcttc agtgaagatg      60
tcctgcaaga cttctggcta cacatttacc agctactgga tgcactgggt aaaacagagg     120
cctggacagg gtctggaatg gatagggct atttatcctg gaaatagtga tactgactac      180
agccagaagt tcaagggcaa ggccacactg actgcagtca catccgccac cactgcctac    240
atggaactca gcagcctgac aaatgaggac tctgcggtct attactgttc aaagtttgac    300
tactggggcc aaggcaccac tctcacagtc tcctca                               336
```

<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Glu Val Gln Leu Gln Gln Ser Gly Thr Val Leu Ala Arg Pro Gly Ala
1               5                   10                  15

Ser Val Lys Met Ser Cys Lys Thr Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Ala Ile Tyr Pro Gly Asn Ser Asp Thr Asp Tyr Ser Gln Lys Phe
        50                  55                  60

Lys Gly Lys Ala Thr Leu Thr Ala Val Thr Ser Ala Thr Thr Ala Tyr
65                  70                  75                  80

Met Glu Leu Ser Ser Leu Thr Asn Glu Asp Ser Ala Val Tyr Tyr Cys
                85                  90                  95

Ser Lys Phe Asp Tyr Trp Gly Gln Gly Thr Thr Leu Thr Val Ser Ser
                100                 105                 110
```

<210> SEQ ID NO 3
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
caaattgttc tcacccagtc tccagcactc atgtctgcat ctccagggga gaaggtcacc      60
```

```
atgacctgca gtgccagctc aagtgtaaat tacatgtact ggtaccagca gaagccaaga      120
tcctccccca aaccctggat ttatctcaca tccaacctgg cttctggagt ccctgctcgc      180
ttcagtggca gggggtctgg gacctcttac tctctcacaa tcagcagcat ggaggctgaa      240
gatgctgcca cttattactg ccagcagtgg agtagtaacc cgtacacgtt cggagggggg      300
accaagctgg aaataaaa                                                    318
```

<210> SEQ ID NO 4
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Asn Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Arg
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Tyr Thr
                85                  90                  95

Phe Gly Gly Gly Thr Lys Leu Glu Ile Lys
            100                 105

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Tyr Trp Met His
1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ile Tyr Pro Gly Asn Ser Asp Thr Asp Tyr Ser Gln Lys Phe Lys
1               5                   10                  15

Gly

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 7

Gly Tyr Thr Phe Thr Ser Tyr
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Pro Gly Asn Ser Asp
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Tyr Thr Phe Thr Ser Tyr Trp
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Tyr Pro Gly Asn Ser Asp Thr
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Lys Phe Asp Tyr
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Ala Ser Ser Ser Val Asn Tyr Met Tyr
1               5                   10

<210> SEQ ID NO 13
<211> LENGTH: 7
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 13

Leu Thr Ser Asn Leu Ala Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Gln Trp Ser Ser Asn Pro Tyr Thr
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Ser Val Asn Tyr
1               5

<210> SEQ ID NO 16
<211> LENGTH: 972
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
gccaaaacga cacccccatc tgtctatcca ctggcccctg gatctgctgc ccaaactaac      60
tccatggtga ccctgggatg cctggtcaag ggctatttcc ctgagccagt gacagtgacc     120
tggaactctg gatccctgtc cagcggtgtg cacaccttcc cagctgtcct gcagtctgac     180
ctctacactc tgagcagctc agtgactgtc ccctccagca cctggcccag ccagaccgtc     240
acctgcaacg ttgcccaccc ggccagcagc accaaggtgg acaagaaaat tgtgcccagg     300
gattgtggtt gtaagccttg catatgtaca gtcccagaag tatcatctgt cttcatcttc     360
cccccaaagc ccaaggatgt gctcaccatt actctgactc ctaaggtcac gtgtgttgtg     420
gtagacatca gcaaggatga tcccgaggtc cagttcagct ggtttgtaga tgatgtggag     480
gtgcacacag ctcagacgca accccgggag gagcagttca cagcactttt ccgctcagtc     540
agtgaacttc ccatcatgca ccaggactgg ctcaatggca aggagttcaa atgcagggtc     600
aacagtgcag ctttccctgc ccccatcgag aaaaccatct ccaaaaccaa aggcagaccg     660
aaggctccac aggtgtacac cattccacct cccaaggagc agatggccaa ggataaagtc     720
agtctgacct gcatgataac agacttcttc cctgaagaca ttactgtgga gtggcagtgg     780
aatgggcagc cagcggagaa ctacaagaac actcagccca tcatggacac agatggctct     840
tacttcgtct acagcaagct caatgtgcag aagagcaact gggaggcagg aaatactttc     900
acctgctctg tgttacatga gggcctgcac aaccaccata ctgagaagag cctctcccac     960

-continued

```
tctcctggta aa                                                      972
```

<210> SEQ ID NO 17
<211> LENGTH: 324
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
                20                  25                  30

Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 18
<211> LENGTH: 321
<212> TYPE: DNA

```
-continued

<213> ORGANISM: Artificial Sequence
<220> FEATURE:
<223> OTHER INFORMATION: Description of Artificial Sequence: Synthetic
      polynucleotide

<400> SEQUENCE: 18
cgggctgatg ctgcaccaac tgtatccatc ttcccaccat ccagtgagca gttaacatct      60
ggaggtgcct cagtcgtgtg cttcttgaac aacttctacc ccagagacat caatgtcaag     120
tggaagattg atggcagtga acgacaaaat ggtgtcctga cagttggac tgatcaggac      180 agcaaagaca gcacctacag catgagcagc accctcacat tgaccaagga cgagtatgaa     240
cgacataaca gctatacctg tgaggccact cacaagacat caacttcacc cattgtcaag     300
agcttcaaca ggaatgagtg t                                                321

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Arg Ala Asp Ala Ala Pro Thr Val Ser Ile Phe Pro Pro Ser Glu
1               5                   10                  15

Gln Leu Thr Ser Gly Gly Ala Ser Val Val Cys Phe Leu Asn Asn Phe
            20                  25                  30

Tyr Pro Arg Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 20
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atggaatgta actggatact tccttttatt ctgtcggtaa cttcaggggt ctactcagag      60
gttcagctcc agcagtctgg gactgtgctg gcaaggcctg ggcttcagt gaagatgtcc      120 tgcaagactt ctggctacac atttaccagc tactggatgc actgggtaaa acagaggcct     180
ggacagggtc tggaatggat agggctatt tatcctggaa atagtgatac tgactacagc      240
cagaagttca gggcaaggc cacactgact gcagtcacat ccgccaccac tgcctacatg      300
gaactcagca gcctgacaaa tgaggactct gcggtctatt actgttcaaa gtttgactac     360
tggggccaag gcaccactct cacagtctcc tcagccaaaa cgacacccc atctgtctat     420 ccactggccc ctgatctgc tgcccaaact aactccatgg tgaccctggg atgcctggtc     480
aagggctatt tccctgagcc agtgacagtg acctggaact ctgatccct gtccagcggt     540
```

```
gtgcacacct tcccagctgt cctgcagtct gacctctaca ctctgagcag ctcagtgact    600 gtccctcca  gcacctggcc cagccagacc gtcacctgca acgttgccca cccggccagc    660
agcaccaagg tggacaagaa aattgtgccc agggattgtg gttgtaagcc ttgcatatgt    720
acagtcccag aagtatcatc tgtcttcatc ttcccccaa  agcccaagga tgtgctcacc    780
attactctga ctcctaaggt cacgtgtgtt gtggtagaca tcagcaagga tgatcccgag    840
gtccagttca gctggtttgt agatgatgtg gaggtgcaca cagctcagac gcaaccccgg    900
gaggagcagt tcaacagcac tttccgctca gtcagtgaac ttcccatcat gcaccaggac    960
tggctcaatg gcaaggagtt caaatgcagg gtcaacagtg cagctttccc tgcccccatc   1020
gagaaaacca tctccaaaac caaaggcaga ccgaaggctc acaggtgta  caccattcca   1080 cctcccaagg agcagatggc caaggataaa gtcagtctga cctgcatgat aacagacttc   1140
ttccctgaag acattactgt ggagtggcag tggaatgggc agccagcgga gaactacaag   1200
aacactcagc ccatcatgga cacagatggc tcttacttcg tctacagcaa gctcaatgtg   1260
cagaagagca actgggaggc aggaaatact ttcacctgct ctgtgttaca tgagggcctg   1320
cacaaccacc atactgagaa gagcctctcc cactctcctg gtaaa                   1365
```

<210> SEQ ID NO 21
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Met Glu Cys Asn Trp Ile Leu Pro Phe Ile Leu Ser Val Thr Ser Gly
1               5                   10                  15

Val Tyr Ser Glu Val Gln Leu Gln Gln Ser Gly Thr Val Leu Ala Arg
            20                  25                  30

Pro Gly Ala Ser Val Lys Met Ser Cys Lys Thr Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Ala Ile Tyr Pro Gly Asn Ser Asp Thr Asp Tyr Ser
65                  70                  75                  80

Gln Lys Phe Lys Gly Lys Ala Thr Leu Thr Ala Val Thr Ser Ala Thr
                85                  90                  95

Thr Ala Tyr Met Glu Leu Ser Ser Leu Thr Asn Glu Asp Ser Ala Val
            100                 105                 110

Tyr Tyr Cys Ser Lys Phe Asp Tyr Trp Gly Gln Gly Thr Thr Leu Thr
        115                 120                 125

Val Ser Ser Ala Lys Thr Thr Pro Pro Ser Val Tyr Pro Leu Ala Pro
    130                 135                 140

Gly Ser Ala Ala Gln Thr Asn Ser Met Val Thr Leu Gly Cys Leu Val
145                 150                 155                 160

Lys Gly Tyr Phe Pro Glu Pro Val Thr Val Thr Trp Asn Ser Gly Ser
                165                 170                 175

Leu Ser Ser Gly Val His Thr Phe Pro Ala Val Leu Gln Ser Asp Leu
            180                 185                 190

Tyr Thr Leu Ser Ser Ser Val Thr Val Pro Ser Ser Thr Trp Pro Ser
        195                 200                 205

Gln Thr Val Thr Cys Asn Val Ala His Pro Ala Ser Ser Thr Lys Val
    210                 215                 220
```

Asp Lys Lys Ile Val Pro Arg Asp Cys Gly Cys Lys Pro Cys Ile Cys
225                 230                 235                 240

Thr Val Pro Glu Val Ser Ser Val Phe Ile Phe Pro Pro Lys Pro Lys
            245                 250                 255

Asp Val Leu Thr Ile Thr Leu Thr Pro Lys Val Thr Cys Val Val Val
            260                 265                 270

Asp Ile Ser Lys Asp Asp Pro Glu Val Gln Phe Ser Trp Phe Val Asp
        275                 280                 285

Asp Val Glu Val His Thr Ala Gln Thr Gln Pro Arg Glu Glu Gln Phe
    290                 295                 300

Asn Ser Thr Phe Arg Ser Val Ser Glu Leu Pro Ile Met His Gln Asp
305                 310                 315                 320

Trp Leu Asn Gly Lys Glu Phe Lys Cys Arg Val Asn Ser Ala Ala Phe
                325                 330                 335

Pro Ala Pro Ile Glu Lys Thr Ile Ser Lys Thr Lys Gly Arg Pro Lys
            340                 345                 350

Ala Pro Gln Val Tyr Thr Ile Pro Pro Lys Glu Gln Met Ala Lys
        355                 360                 365

Asp Lys Val Ser Leu Thr Cys Met Ile Thr Asp Phe Phe Pro Glu Asp
370                 375                 380

Ile Thr Val Glu Trp Gln Trp Asn Gly Gln Pro Ala Glu Asn Tyr Lys
385                 390                 395                 400

Asn Thr Gln Pro Ile Met Asp Thr Asp Gly Ser Tyr Phe Val Tyr Ser
            405                 410                 415

Lys Leu Asn Val Gln Lys Ser Asn Trp Glu Ala Gly Asn Thr Phe Thr
            420                 425                 430

Cys Ser Val Leu His Glu Gly Leu His Asn His Thr Glu Lys Ser
        435                 440                 445

Leu Ser His Ser Pro Gly Lys
    450                 455

<210> SEQ ID NO 22
<211> LENGTH: 705
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 22
atggattttc aagtgcagat tttcagcttc ctgctaatga gtgcctcagt cataatgtcc      60
aggggacaaa ttgttctcac ccagtctcca gcactcatgt ctgcatctcc aggggagaag     120
gtcaccatga cctgcagtgc cagctcaagt gtaaattaca tgtactggta ccagcagaag     180
ccaagatcct cccccaaacc ctggatttat ctcacatcca acctggcttc tggagtccct     240
gctcgcttca gtggcagggg gtctgggacc tcttactctc tcacaatcag cagcatggag     300
gctgaagatg ctgccactta ttactgccag cagtggagta gtaacccgta cacgttcgga     360
gggggaacca agctggaaat aaaacgggct gatgctgcac caactgtatc catcttccca     420
ccatccagtg agcagttaac atctggaggt gcctcagtcg tgtgcttctt gaacaacttc     480
taccccagag acatcaatgt caagtggaag attgatggca gtgaacgaca aaatggtgtc     540
ctgaacagtt ggactgatca ggacagcaaa gacagcacct acagcatgag cagcaccctc     600
acattgacca aggacgagta tgaacgacat aacagctata cctgtgaggc cactcacaag     660
acatcaactt cacccattgt caagagcttc aacaggaatg agtgt               705

<210> SEQ ID NO 23
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Asp Phe Gln Val Gln Ile Phe Ser Phe Leu Leu Met Ser Ala Ser
1               5                   10                  15

Val Ile Met Ser Arg Gly Gln Ile Val Leu Thr Gln Ser Pro Ala Leu
            20                  25                  30

Met Ser Ala Ser Pro Gly Glu Lys Val Thr Met Thr Cys Ser Ala Ser
        35                  40                  45

Ser Ser Val Asn Tyr Met Tyr Trp Tyr Gln Gln Lys Pro Arg Ser Ser
    50                  55                  60

Pro Lys Pro Trp Ile Tyr Leu Thr Ser Asn Leu Ala Ser Gly Val Pro
65                  70                  75                  80

Ala Arg Phe Ser Gly Arg Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser Asn Pro Tyr Thr Phe Gly Gly Gly Thr Lys Leu Glu Ile Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Arg Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
acttgggctg gagtgatttg                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aatcccatct gcacacttcc                                          20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
caaaaacatg gctgagcaga                                          20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaaacaggcc ccactttgta                                          20

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctaatacgac tcactatagg gcaagcagtg gtatcaacgc agagt              45

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctaatacgac tcactatagg gc                                       22

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tatgcaaggc ttacaaccac a                                        21

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cgactgaggc acctccagat gtt                                      23

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtaaaacgac ggccagt                                                        17

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
caggaaacag ctatgacc                                                       18

<210> SEQ ID NO 34
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
caagtgcagc tcgtccaatc gggagccgaa gtgaagaagc tggttcctc ggtaaaagta         60 agctgtaagg cgtccggtta cacgtttacc tcatattgga tgcactgggt cagacaggca       120
cccggacagg gactcgagtg gatgggagcg atctacccgg gcaattcgga cactgattac       180
agccagaaat tcaaggggag ggtcacgatc acggcagatg agagcacatc aacagcctat       240
atggagctgt cgtcgcttcg gagcgaggac acggcggtct actactgctc caaattcgac       300
tattgggggc aggggacctt ggtgaccgtg tcatcc                                  336

<210> SEQ ID NO 35
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Ala Ile Tyr Pro Gly Asn Ser Asp Thr Asp Tyr Ser Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Lys Phe Asp Tyr Trp Gly Gln Gly Thr Leu Val Thr Val Ser Ser

<210> SEQ ID NO 36
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
caagtgcagc tcgtccaatc gggagccgaa gtgaagaagc ctggttcctc ggtaaaagta      60
agctgtaagg cgtccggtta cacgtttttcc tcatattgga tgcactgggt cagacaggca   120
cccggacagg gactcgagtg gatgggagcg atctacccgg gcaattcgga cactgattac   180
agccagaaat tccaggggag ggtcacgatc acggcagatg agagcacatc aacagcctat   240
atggagctgt cgtcgcttcg gagcgaggac acggcggtct actactgctc caaattcgac   300
tattgggggc aggggacctt ggtgaccgtg tcatcc                              336
```

<210> SEQ ID NO 37
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Gln Val Gln Leu Val Gln Ser Gly Ala Glu Val Lys Lys Pro Gly Ser
 1               5                  10                  15
Ser Val Lys Val Ser Cys Lys Ala Ser Gly Tyr Thr Phe Ser Ser Tyr
                20                  25                  30
Trp Met His Trp Val Arg Gln Ala Pro Gly Gln Gly Leu Glu Trp Met
            35                  40                  45
Gly Ala Ile Tyr Pro Gly Asn Ser Asp Thr Asp Tyr Ser Gln Lys Phe
        50                  55                  60
Gln Gly Arg Val Thr Ile Thr Ala Asp Glu Ser Thr Ser Thr Ala Tyr
 65                 70                  75                  80
Met Glu Leu Ser Ser Leu Arg Ser Glu Asp Thr Ala Val Tyr Tyr Cys
                85                  90                  95
Ser Lys Phe Asp Tyr Trp Gly Gln Gly Thr Leu Val Thr Val Ser Ser
               100                 105                 110
```

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

```
Ala Ile Tyr Pro Gly Asn Ser Asp Thr Asp Tyr Ser Gln Lys Phe Gln
 1               5                  10                  15
Gly
```

<210> SEQ ID NO 39
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

```
gaaattgtgc tgacccagag cccggcgacc ctgagcctga gcccgggcga acgcgcgacc    60
ctgagctgcc gcgcgagcag cagcgtgaac tatatgtatt ggtatcagca gaaaccgggc   120
caggcgccgc gcccgtggat ttatctgacc agcaaccgcg cgaccggcgt gccggcgcgc   180
tttagcggca gcggcagcgg caccgattat accctgacca ttagcagcct ggaaccggaa   240
gattttgcgg tgtattattg ccagcagtgg agcagcaacc cgtataccct tggccagggc   300
accaaactgg aaattaaa                                                 318
```

<210> SEQ ID NO 40
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Asn Tyr Met
            20                  25                  30

Tyr Trp Tyr Gln Gln Lys Pro Gly Gln Ala Pro Arg Pro Trp Ile Tyr
        35                  40                  45

Leu Thr Ser Asn Arg Ala Thr Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Tyr Thr
                85                  90                  95

Phe Gly Gln Gly Thr Lys Leu Glu Ile Lys
            100                 105

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ala Ser Ser Ser Val Asn Tyr Met Tyr
1               5                   10

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Thr Ser Asn Arg Ala Thr
1               5

<210> SEQ ID NO 43
<211> LENGTH: 318
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 43
gaaatcgtac ttactcagag ccctgccaca ttgtcattgt cacccgggga acgcgccaca      60
ctgtcgtgcc gggcttcatc gagcgtgaac tacatgtatt ggtatcaaca gaaaccaggc     120
caagcaccgc gaccttggat ctacttgacg agcaatcgag ccacgggtat ccccgcgagg     180
ttctccggtt cggggtcggg aactgattac acactgacaa tttcctcgct ggagcccgag     240
gacttcgcgg tgtactattg tcagcagtgg tcatccaacc cgtacacgtt tggacagggg     300
acgaagctcg agatcaag                                                   318

<210> SEQ ID NO 44
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Asn Tyr Met
            20                  25                  30

Tyr Trp Tyr Gln Gln Lys Pro Gly Gln Ala Pro Arg Pro Trp Ile Tyr
        35                  40                  45

Leu Thr Ser Asn Arg Ala Thr Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Tyr Thr
                85                  90                  95

Phe Gly Gln Gly Thr Lys Leu Glu Ile Lys
            100                 105

<210> SEQ ID NO 45
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
gaaatcgtac ttactcagag ccctgccaca ttgtcattgt cacccgggga acgcgccaca      60
ctgtcgtgcc gggcttcatc gagcgtgaac tacatgtatt ggtatcaaca gaaaccaggc     120
caagcaccgc gaccttggat ctacttgacg agcaatcgag ccacgggtat ccccgcgagg     180
ttctccggtt cggggtcggg aactgatttc acactgacaa tttcctcgct ggagcccgag    240
gacttcgcgg tgtactattg tcagcagtgg tcatccaacc cgtacacgtt tggacagggg     300
acgaagctcg agatcaag                                                   318

<210> SEQ ID NO 46
<211> LENGTH: 106
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Asn Tyr Met
            20                  25                  30

Tyr Trp Tyr Gln Gln Lys Pro Gly Gln Ala Pro Arg Pro Trp Ile Tyr
        35                  40                  45

Leu Thr Ser Asn Arg Ala Thr Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Tyr Thr
                85                  90                  95

Phe Gly Gln Gly Thr Lys Leu Glu Ile Lys
            100                 105

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Gly Tyr Thr Phe Ser Ser Tyr
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Gly Tyr Thr Phe Ser Ser Tyr Trp
1               5

<210> SEQ ID NO 49
<211> LENGTH: 990
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 49
gcctcaacaa aaggaccaag tgtgttccca ctcgccccta gcagcaagag tacatccggg      60
ggcactgcag cactcggctg cctcgtcaag gattattttc cagagccagt aaccgtgagc     120
tggaacagtg gagcactcac ttctggtgtc catactttc ctgctgtcct gcaaagctct      180
ggcctgtact cactcagctc cgtcgtgacc gtgccatctt catctctggg cactcagacc     240
tacatctgta atgtaaacca caagcctagc aatactaagg tcgataagcg ggtggaaccc     300
aagagctgcg acaagactca cacttgtccc ccatgccctg ccctgaact tctgggcggt      360 cccagcgtct ttttgttccc accaaagcct aaagatactc tgatgataag tagaacaccc     420
gaggtgacat gtgttgttgt agacgtttcc cacgaggacc cagaggttaa gttcaactgg     480

```
tacgttgatg agtcgaagt acataatgct aagaccaagc ctagagagga gcagtataat      540
agtacatacc gtgtagtcag tgttctcaca gtgctgcacc aagactggct caacggcaaa      600
gaatacaaat gcaaagtgtc caacaaagca ctcccagccc ctatcgagaa gactattagt      660
aaggcaaagg ggcagcctcg tgaaccacag gtgtacactc tgccacccag tagagaggaa      720
atgacaaaga accaagtctc attgacctgc ctggtgaaag cttctaccc cagcgacatc       780 gccgttgagt gggagagtaa cggtcagcct gagaacaatt acaagacaac ccccccagtg      840
ctggatagtg acgggtcttt ctttctgtac agtaagctga ctgtggacaa gtcccgctgg      900
cagcagggta acgtcttcag ctgttccgtg atgcacgagg cattgcacaa ccactacacc      960
cagaagtcac tgagcctgag cccagggaag                                       990
```

<210> SEQ ID NO 50
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 51
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
cgcacagttg ctgcccccag cgtgttcatt ttcccaccta gcgatgagca gctgaaaagc      60
ggtactgcct ctgtcgtatg cttgctcaac aacttttacc cacgtgaggc taaggtgcag     120
tggaaagtgg ataatgcact tcaatctgga aacagtcaag agtccgtgac agaacaggac     180
agcaaagact caacttattc actctcttcc accctgactc tgtccaaggc agactatgaa     240
aaacacaagg tatacgcctg cgaggttaca caccagggtt tgtctagtcc tgtcaccaag     300
tccttcaata ggggcgaatg t                                              321

<210> SEQ ID NO 52
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 53
<211> LENGTH: 1392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
atggacatga gagttcctgc tcagctgctc gggttgctgt tgctttggct ccggggtgct      60

```
aggtgccaag tgcagctcgt ccaatcggga gccgaagtga agaagcctgg ttcctcggta    120
aaagtaagct gtaaggcgtc cggttacacg tttacctcat attggatgca ctgggtcaga    180
caggcacccg gacagggact cgagtggatg ggagcgatct acccgggcaa ttcggacact    240
gattacagcc agaaattcaa ggggagggtc acgatcacgg cagatgagag cacatcaaca    300
gcctatatgg agctgtcgtc gcttcggagc gaggacacgg cggtctacta ctgctccaaa    360
ttcgactatt gggggcaggg gaccttggtg accgtgtcat ccgcctcaac aaaaggacca    420
agtgtgttcc cactcgcccc tagcagcaag agtacatccg gggcactgc agcactcggc     480
tgcctcgtca aggattattt tccagagcca gtaaccgtga gctggaacag tggagcactc    540
acttctggtg tccatacttt tcctgctgtc ctgcaaagct ctggcctgta ctcactcagc    600
tccgtcgtga ccgtgccatc ttcatctctg ggcactcaga cctacatctg taatgtaaac    660
cacaagccta gcaatactaa ggtcgataag cgggtggaac ccaagagctg cgacaagact    720
cacacttgtc ccccatgccc tgcccctgaa cttctgggcg gtcccagcgt cttttgttc    780
ccaccaaagc ctaaagatac tctgatgata agtagaacac ccgaggtgac atgtgttgtt    840
gtagacgttt cccacgagga cccagaggtt aagttcaact ggtacgttga tggagtcgaa    900
gtacataatg ctaagaccaa gcctagagag gagcagtata atagtacata ccgtgtagtc    960
agtgttctca cagtgctgca ccaagactgg ctcaacggca agaatacaa atgcaaagtg    1020
tccaacaaag cactcccagc ccctatcgag aagactatta gtaaggcaaa ggggcagcct    1080
cgtgaaccac aggtgtacac tctgccaccc agtagagagg aaatgacaaa gaaccaagtc    1140
tcattgacct gcctggtgaa aggcttctac cccagcgaca tcgccgttga gtgggagagt    1200
aacggtcagc ctgagaacaa ttacaagaca accccccag tgctggatag tgacgggtct    1260
ttctttctgt acagtaagct gactgtggac aagtcccgct ggcagcaggg taacgtcttc    1320
agctgttccg tgatgcacga ggcattgcac aaccactaca cccagaagtc actgagcctg    1380
agcccaggga ag                                                        1392
```

<210> SEQ ID NO 54
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Tyr Thr Phe Thr Ser Tyr Trp Met His Trp Val Arg Gln Ala Pro Gly
    50                  55                  60

Gln Gly Leu Glu Trp Met Gly Ala Ile Tyr Pro Gly Asn Ser Asp Thr
65                  70                  75                  80

Asp Tyr Ser Gln Lys Phe Lys Gly Arg Val Thr Ile Thr Ala Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ser Lys Phe Asp Tyr Trp Gly Gln Gly Thr
```

```
                    115                 120                 125
Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
210                 215                 220

Asn Thr Lys Val Asp Lys Arg Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
450                 455                 460

<210> SEQ ID NO 55
<211> LENGTH: 1392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
atggacatga gagttcctgc tcagctgctc gggttgctgt tgctttggct ccggggtgct       60
aggtgccaag tgcagctcgt ccaatcggga gccgaagtga agaagcctgg ttcctcggta      120
```

```
aaagtaagct gtaaggcgtc cggttacacg ttttcctcat attggatgca ctgggtcaga    180
caggcacccg acagggact cgagtggatg ggagcgatct acccgggcaa ttcggacact    240
gattacagcc agaaattcca ggggagggtc acgatcacgg cagatgagag cacatcaaca    300
gcctatatgg agctgtcgtc gcttcggagc gaggacacgg cggtctacta ctgctccaaa    360
ttcgactatt gggggcaggg gaccttggtg accgtgtcat ccgcctcaac aaaaggacca    420
agtgtgttcc cactcgcccc tagcagcaag agtacatccg ggggcactgc agcactcggc    480
tgcctcgtca aggattattt tccagagcca gtaaccgtga gctggaacag tggagcactc    540
acttctggtg tccatacttt tcctgctgtc ctgcaaagct ctggcctgta ctcactcagc    600
tccgtcgtga ccgtgccatc ttcatctctg gcactcaga cctacatctg taatgtaaac    660
cacaagccta gcaatactaa ggtcgataag cgggtggaac ccaagagctg cgacaagact    720
cacacttgtc ccccatgccc tgcccctgaa cttctgggcg gtcccagcgt cttttttgttc    780
ccaccaaagc ctaaagatac tctgatgata agtagaacac ccgaggtgac atgtgttgtt    840
gtagacgttt cccacgagga cccagaggtt aagttcaact ggtacgttga tggagtcgaa    900
gtacataatg ctaagaccaa gcctagagag gagcagtata atagtacata ccgtgtagtc    960
agtgttctca cagtgctgca ccaagactgg ctcaacggca agaatacaa atgcaaagtg   1020
tccaacaaag cactcccagc ccctatcgag aagactatta gtaaggcaaa ggggcagcct   1080
cgtgaaccac aggtgtacac tctgccaccc agtagagagg aaatgacaaa gaaccaagtc   1140
tcattgacct gcctggtgaa aggcttctac cccagcgaca cgccgttga gtgggagagt   1200
aacggtcagc ctgagaacaa ttacaagaca accccccag tgctggatag tgacgggtct   1260
ttctttctgt acagtaagct gactgtggac aagtcccgct ggcagcaggg taacgtcttc   1320
agctgttccg tgatgcacga ggcattgcac aaccactaca cccagaagtc actgagcctg   1380
agcccaggga ag                                                       1392
```

<210> SEQ ID NO 56
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Tyr Thr Phe Ser Ser Tyr Trp Met His Trp Val Arg Gln Ala Pro Gly
    50                  55                  60

Gln Gly Leu Glu Trp Met Gly Ala Ile Tyr Pro Gly Asn Ser Asp Thr
65                  70                  75                  80

Asp Tyr Ser Gln Lys Phe Gln Gly Arg Val Thr Ile Thr Ala Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ser Lys Phe Asp Tyr Trp Gly Gln Gly Thr
        115                 120                 125

Leu Val Thr Val Ser Ser Ala Ser Thr Lys Gly Pro Ser Val Phe Pro
```

```
                130             135             140
Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
210                 215                 220

Asn Thr Lys Val Asp Lys Arg Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
450                 455                 460

<210> SEQ ID NO 57
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
atggacatga gggtgcccgc tcaactgctg gggctgctgc tgctgtggct gagaggagct      60
cgttgcgaaa ttgtgctgac ccagagcccg gcgaccctga gcctgagccc gggcgaacgc     120
gcgaccctga gctgccgcgc gagcagcagc gtgaactata tgtattggta tcagcagaaa     180
ccgggccagg cgccgcgccc gtggatttat ctgaccagca accgcgcgac cggcgtgccg     240
```

```
gcgcgcttta gcggcagcgg cagcggcacc gattataccc tgaccattag cagcctggaa    300
ccggaagatt ttgcggtgta ttattgccag cagtggagca gcaacccgta tacctttggc    360
cagggcacca aactggaaat taaacgcaca gttgctgccc ccagcgtgtt cattttccca    420
cctagcgatg agcagctgaa agcggtact  gcctctgtcg tatgcttgct caacaacttt    480
tacccacgtg aggctaaggt gcagtggaaa gtggataatg cacttcaatc tggaaacagt    540
caagagtccg tgacagaaca ggacagcaaa gactcaactt attcactctc ttccaccctg    600
actctgtcca aggcagacta tgaaaaacac aaggtatacg cctgcgaggt tacacaccag    660
ggtttgtcta gtcctgtcac caagtccttc aatagggggcg aatgt                  705
```

<210> SEQ ID NO 58
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Met Asp Met Arg Val Pro Ala Gln Leu Leu Gly Leu Leu Leu Leu Trp
1               5                   10                  15

Leu Arg Gly Ala Arg Cys Glu Ile Val Leu Thr Gln Ser Pro Ala Thr
            20                  25                  30

Leu Ser Leu Ser Pro Gly Glu Arg Ala Thr Leu Ser Cys Arg Ala Ser
        35                  40                  45

Ser Ser Val Asn Tyr Met Tyr Trp Tyr Gln Gln Lys Pro Gly Gln Ala
    50                  55                  60

Pro Arg Pro Trp Ile Tyr Leu Thr Ser Asn Arg Ala Thr Gly Val Pro
65                  70                  75                  80

Ala Arg Phe Ser Gly Ser Gly Ser Gly Thr Asp Tyr Thr Leu Thr Ile
                85                  90                  95

Ser Ser Leu Glu Pro Glu Asp Phe Ala Val Tyr Tyr Cys Gln Gln Trp
            100                 105                 110

Ser Ser Asn Pro Tyr Thr Phe Gly Gln Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 59
<211> LENGTH: 705
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59

```
atggacatga gggtgcccgc tcaactgctg gggctgctgc tgctgtggct gagaggagct      60
cgttgcgaaa tcgtacttac tcagagccct gccacattgt cattgtcacc cggggaacgc     120
gccacactgt cgtgccgggc ttcatcgagc gtgaactaca tgtattggta tcaacagaaa     180
ccaggccaag caccgcgacc ttggatctac ttgacgagca atcgagccac gggtatcccc     240
gcgaggttct ccggttcggg gtcgggaact gattacacac tgacaatttc ctcgctggag     300
cccgaggact tcgcggtgta ctattgtcag cagtggtcat ccaacccgta cacgtttgga     360
caggggacga agctcgagat caagcgcaca gttgctgccc cagcgtgtt cattttccca      420
cctagcgatg agcagctgaa aagcggtact gcctctgtcg tatgcttgct caacaacttt     480
tacccacgtg aggctaaggt gcagtggaaa gtggataatg cacttcaatc tggaaacagt     540
caagagtccg tgacagaaca ggacagcaaa gactcaactt attcactctc ttccaccctg     600
actctgtcca aggcagacta tgaaaaacac aaggtatacg cctgcgaggt tacacaccag     660
ggtttgtcta gtcctgtcac caagtccttc aataggggcg aatgt                    705
```

<210> SEQ ID NO 60
<211> LENGTH: 235
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

```
Met Asp Met Arg Val Pro Ala Gln Leu Leu Gly Leu Leu Leu Leu Trp
1               5                   10                  15

Leu Arg Gly Ala Arg Cys Glu Ile Val Leu Thr Gln Ser Pro Ala Thr
            20                  25                  30

Leu Ser Leu Ser Pro Gly Glu Arg Ala Thr Leu Ser Cys Arg Ala Ser
        35                  40                  45

Ser Ser Val Asn Tyr Met Tyr Trp Tyr Gln Gln Lys Pro Gly Gln Ala
    50                  55                  60

Pro Arg Pro Trp Ile Tyr Leu Thr Ser Asn Arg Ala Thr Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Glu Pro Glu Asp Phe Ala Val Tyr Tyr Cys Gln Gln Trp
            100                 105                 110

Ser Ser Asn Pro Tyr Thr Phe Gly Gln Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220
```

Pro Val Thr Lys Ser Phe Asn Arg Gly Glu Cys
225                 230                 235

<210> SEQ ID NO 61
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
atggacatga gggtgcccgc tcaactgctg gggctgctgc tgctgtggct gagaggagct      60
cgttgcgaaa tcgtacttac tcagagccct gccacattgt cattgtcacc cggggaacgc     120
gccacactgt cgtgccgggc ttcatcgagc gtgaactaca tgtattggta tcaacagaaa     180
ccaggccaag caccgcgacc ttggatctac ttgacgagca atcgagccac gggtatcccc     240
gcgaggttct ccggttcggg gtcgggaact gatttcacac tgacaatttc ctcgctggag     300
cccgaggact tcgcggtgta ctattgtcag cagtggtcat ccaacccgta cacgtttgga     360
caggggacga agctcgagat caagcgcaca gttgctgccc cagcgtgtt cattttccca     420 cctagcgatg agcagctgaa aagcggtact gcctctgtcg tatgcttgct caacaacttt     480
tacccacgtg aggctaaggt gcagtggaaa gtggataatg cacttcaatc tggaaacagt     540
caagagtccg tgacagaaca ggacagcaaa gactcaactt attcactctc ttccaccctg     600
actctgtcca aggcagacta tgaaaaacac aaggtatacg cctgcgaggt tacacaccag     660
ggtttgtcta gtcctgtcac caagtccttc aatagggcg aatgt                      705

<210> SEQ ID NO 62
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Asp Met Arg Val Pro Ala Gln Leu Leu Gly Leu Leu Leu Leu Trp
1               5                   10                  15

Leu Arg Gly Ala Arg Cys Glu Ile Val Leu Thr Gln Ser Pro Ala Thr
                20                  25                  30

Leu Ser Leu Ser Pro Gly Glu Arg Ala Thr Leu Ser Cys Arg Ala Ser
            35                  40                  45

Ser Ser Val Asn Tyr Met Tyr Trp Tyr Gln Gln Lys Pro Gly Gln Ala
        50                  55                  60

Pro Arg Pro Trp Ile Tyr Leu Thr Ser Asn Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Trp
            100                 105                 110

Ser Ser Asn Pro Tyr Thr Phe Gly Gln Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

-continued

```
Tyr Pro Arg Glu Ala Lys Val Gln Trp Lys Val Asp Asn Ala Leu Gln
            165             170             175

Ser Gly Asn Ser Gln Glu Ser Val Thr Glu Gln Asp Ser Lys Asp Ser
        180             185             190

Thr Tyr Ser Leu Ser Ser Thr Leu Thr Leu Ser Lys Ala Asp Tyr Glu
        195             200             205

Lys His Lys Val Tyr Ala Cys Glu Val Thr His Gln Gly Leu Ser Ser
    210             215             220

Pro Val Thr Lys Ser Phe Asn Arg Gly Glu Cys
225             230             235
```

ANTI-FGFR2 ANTIBODIES

CROSS-REFERENCE TO RELATED APPLICATION

This application claims the benefit of and priority to U.S. Provisional Application Ser. No. 61/333,590, filed May 11, 2010; the content of which is incorporated herein in its entirety.

SEQUENCE LISTING

The instant application contains a Sequence Listing which has been submitted in ASCII format via EFS-Web and is hereby incorporated by reference in its entirety. Said ASCII copy, created on Jun. 16, 2011, is named AVO016US.txt and is 61,526 bytes in size.

FIELD OF THE INVENTION

The field of the invention is molecular biology, immunology and oncology. More particularly, the field is antibodies that bind human FGFR2.

BACKGROUND

Fibroblast Growth Factor Receptor 2 (FGFR2), also known as BEK, BFR-1, CD332, CEK3, CFD1, ECT1, FLJ98662, JWS, KGFR (also known as FGFR2(IIIb)), K-SAM, TK14, and TK25, is one of four highly conserved receptor tyrosine kinases (FGFR1, FGFR2, FGFR3 and FGFR4) that mediate fibroblast growth factor (FGF) signaling by binding FGFs. The FGF receptors are characterized by two or three extracellular immunoglobulin-like domains (IgD1, IgD2 and IgD3), a single-pass transmembrane domain, and a cytoplasmic tyrosine kinase domain. FGF ligand binding induces FGF receptor dimerization and tyrosine autophosphorylation, resulting in cell proliferation, differentiation and migration (Turner et al. (2010) NATURE REVIEWS CANCER 10:116-129; Beenken et al. (2009) NATURE REVIEWS DRUG DISCOVERY 8:235-254; Gomez-Roman et al. (2005) CLIN. CANCER RES. 11:459-65; Chang et al. (2005) BLOOD 106:353-6; Eswarakumar et al. (2005) CYTOKINE GROWTH FACTOR REV. 16:139-49).

Alternative splicing in the IgD3 domain yields either the IIIb or IIIc isoform of FGFR1, FGFR2 and FGFR3. The FGFR4 gene is expressed only as the IIIc isoform. The different isoforms of FGF receptors exhibit tissue-specific expression, and they respond to a different spectrum of 18 mammalian FGFs (Beenken et al., supra). Binding of FGFs to FGFRs in the presence of heparan sulfate proteoglycans induces autophosphorylation of FGFRs at specific intracellular tyrosine residues. This causes phosphorylation of adaptor molecules, such as FGFR substrate $2\alpha$ (FRS2$\alpha$), which recruits other proteins to activate various signaling cascades, including the mitogen-activated protein kinase (MAPK) pathway and the phosphoinositide 3-kinase (PI3K)/Akt pathway (Beenken et al., supra; Eswarakumar et al., supra; Turner et al., supra).

It has been suggested that the dysregulated FGF signaling can directly drive the proliferation of cancer cells, promote the survival of cancer stem cells, and support tumor angiogenesis (Turner et al., supra). FGFR2 signaling appears to play a role in cancer. Missense mutations in the FGFR2 gene occur in various cancers, including endometrial cancer (Pollock et al., 2007, ONCOGENE 26:7158-7162; Dutt et al., 2008, PROC. NATL. ACAD. SCI. USA 105:8713-8717), ovarian cancer, breast cancer, lung cancer (Greenman et al., 2007, Nature 446:153-158; Ding et al., 2008, NATURE 455:1069-1075; Davies et al., 2005, CANCER RES. 65:7591-7595) and gastric cancer (Jang et al., 2001, CANCER RES. 61:3541-3543). Some of these activating mutations also have been reported in patients with skeletal disorders (Dutt et al., supra). Two independent genome-wide association studies have linked specific single nucleotide polymorphisms (SNPs) in the FGFR2 gene to increased susceptibility to breast cancer (Easton et al., 2007, NATURE 447:1087-1093; Hunter et al., 2007, NAT. GENET. 39:870-874). These cancer-associated SNPs appear to elevate FGFR2 gene expression (Meyer et al., 2008, PLOS BIOL. 6:e108). The FGFR2 gene, located at human chromosome 10q26, is amplified in a subset of breast cancers (Adnane et al., 1991, ONCOGENE 6:659-663; Turner et al., 2010, ONCOGENE 29:2013-2023) and gastric cancer (Hara et al., 1998, LAB. INVEST. 78:1143-1153; Mor et al., 1993, CANCER GENET. CYTOGENET. 65:111-114).

Naturally occurring antibodies are multimeric proteins that contain four polypeptide chains (FIG. 1). Two of the polypeptide chains are called immunoglobulin heavy chains (H chains), and two of the polypeptide chains are called immunoglobulin light chains (L chains). The immunoglobulin heavy and light chains are connected by an interchain disulfide bond. The immunoglobulin heavy chains are connected by interchain disulfide bonds. A light chain consists of one variable region ($V_L$ in FIG. 1) and one constant region ($C_L$ in FIG. 1). The heavy chain consists of one variable region ($V_H$ in FIG. 1) and at least three constant regions ($CH_1$, $CH_2$ and $CH_3$ in FIG. 1). The variable regions determine the specificity of the antibody. Naturally occurring antibodies have been used as starting material for engineered antibodies, such as chimeric antibodies and humanized antibodies.

Each variable region contains three hypervariable regions known as complementarity determining regions (CDRs) flanked by four relatively conserved regions known as framework regions (FRs). The three CDRs, referred to as $CDR_1$, $CDR_2$, and $CDR_3$, contribute to the antibody binding specificity.

Inhibitory antibodies specific against human FGFR2 have been difficult to generate because of the high homology between mouse and human FGFR2. In particular, the ligand binding domain of the mouse and human FGFR2 shares approximately 98% sequence identity (Wei et al., 2006, HYBRIDOMA 25:115-124). Thus, there is a need for improved FGFR2 antibodies that can be used as therapeutic agents.

SUMMARY OF THE INVENTION

The invention is based on the discovery of a family of antibodies that specifically bind human FGFR2. The antibodies contain FGFR2 binding sites based on the CDRs of an antibody that specifically binds FGFR2. When used as therapeutic agents, the antibodies are engineered, e.g., humanized, to reduce or eliminate an immune response when administered to a human patient.

The antibodies of the invention prevent or inhibit the activation of (i.e., neutralize) human FGFR2. The antibodies of the invention can be used to inhibit the proliferation of tumor cells in vitro or in vivo. When administered to a human cancer patient (or an animal model), the antibodies inhibit or reduce tumor growth in the human patient (or animal model).

These and other aspects and advantages of the invention are illustrated by the following figures, detailed description and claims. As used herein, "including" means without limitation, and examples cited are non-limiting.

DESCRIPTION OF THE DRAWINGS

The invention can be more completely understood with reference to the following drawings.

FIG. 8 is a schematic diagram showing the amino acid sequences of the complete murine immunoglobulin heavy chain variable region of 4B9 (SEQ ID NO: 2) and the complete humanized heavy chain variable regions denoted as Hu4B9-65 (SEQ ID NO: 35) and Hu4B9-82, -83 (SEQ ID NO: 37). The amino acid sequences for each heavy chain variable region are aligned against one another, and Complementary Determining Sequences (CDR) (Kabat definition), $CDR_1$, $CDR_2$, and $CDR_3$, are identified in boxes. The unboxed sequences represent framework (FR) sequences.

FIG. 9 is a schematic diagram showing the $CDR_1$, $CDR_2$, and $CDR_3$ sequences (Kabat definition) for each of the variable region sequences shown in FIG. 8.

FIG. 10 is a schematic diagram showing the amino acid sequences of the complete murine immunoglobulin light chain variable region of 4B9 (SEQ ID NO: 4) and the complete humanized light chain variable regions denoted as Hu4B9-65 (SEQ ID NO: 40), Hu4B9-82 (SEQ ID NO: 44), and Hu4B9-83 (SEQ ID NO: 46). The amino acid sequences for each light chain variable region are aligned against one another, and $CDR_1$, $CDR_2$, and $CDR_3$ sequences (Kabat definition) are identified in boxes. The unboxed sequences represent framework (FR) sequences.

FIG. 11 is a schematic diagram showing the $CDR_1$, $CDR_2$, and $CDR_3$ sequences (Kabat definition) for each of the variable region sequences shown in FIG. 10.

DETAILED DESCRIPTION

Figure 1:
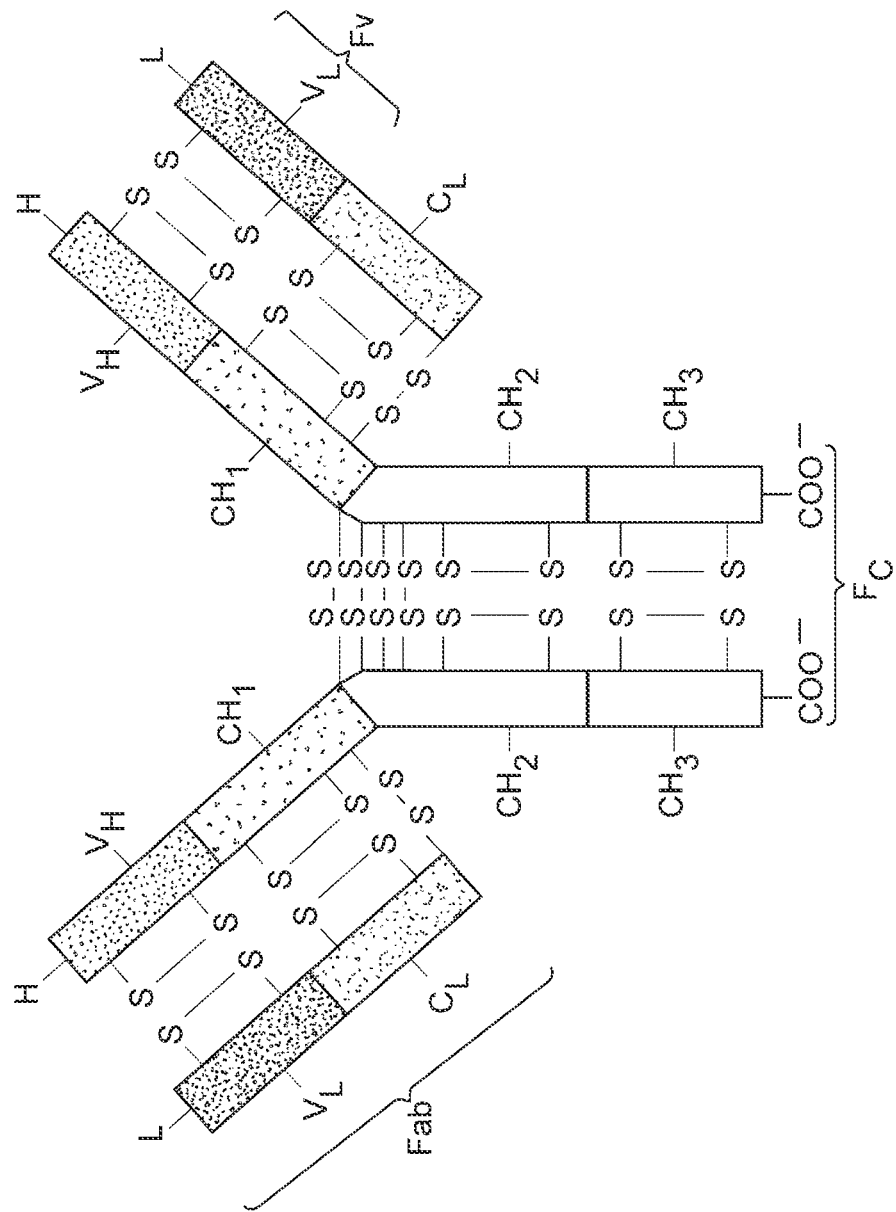
FIG. 1 (prior art) is a schematic representation of a typical antibody.

The FGFR2 antibodies of the invention are based on the antigen binding sites of a monoclonal antibody selected on the basis of neutralizing the biological activity of human FGFR2 polypeptides. The antibodies contain immunoglobulin variable region CDR sequences that define a binding site for human FGFR2.

Because of the neutralizing activity of these antibodies, they are useful for inhibiting the growth and/or proliferation of certain cancer cells and tumors. The antibodies can be engineered to minimize or eliminate an immune response when administered to a human patient. Various features and aspects of the invention are discussed in more detail below.

As used herein, unless otherwise indicated, the term "antibody" means an intact antibody (e.g., an intact monoclonal antibody) or antigen-binding fragment of an antibody (e.g., an antigen-binding fragment of a monoclonal antibody), including an intact antibody or antigen-binding fragment that has been modified, engineered or chemically conjugated. Examples of antibodies that have been modified or engineered are chimeric antibodies, humanized antibodies, and multispecific antibodies (e.g., bispecific antibodies). Examples of antigen-binding fragments include Fab, Fab', $F(ab')_2$, Fv, single chain antibodies (e.g., scFv) and diabodies. An antibody conjugated to a toxin moiety is an example of a chemically conjugated antibody.

Antibodies that Bind Human FGFR2

Antibodies of the invention comprise: (a) an immunoglobulin heavy chain variable region comprising the structure $CDR_{H1}$-$CDR_{H2}$-$CDR_{H3}$ and (b) an immunoglobulin light chain variable region comprising the structure $CDR_{L1}$-$CDR_{L2}$-$CDR_{L3}$, wherein the heavy chain variable region and the light chain variable region together define a single binding site for binding human FGFR2.

As disclosed herein, an antibody may comprise: (a) an immunoglobulin heavy chain variable region comprising the structure $CDR_{H1}$-$CDR_{H2}$-$CDR_{H3}$ and (b) immunoglobulin light chain variable region, wherein the heavy chain variable region and the light chain variable region together define a single binding site for binding human FGFR2. A $CDR_{H1}$ comprises an amino acid sequence selected from the group consisting of SEQ ID NO: 5 (4B9; Hu4B9-65; Hu4B9-82, -83), SEQ ID NO: 7 (4B9; Hu4B9-65), and SEQ ID NO: 47 (Hu4B9-82, -83); a $CDR_{H2}$ comprises an amino acid sequence selected from the group consisting of SEQ ID NO: 6 (4B9; Hu4B9-65) and SEQ ID NO: 38 (Hu4B9-82, -83); and a $CDR_{H3}$ comprises an amino acid sequence selected from the group consisting of amino acid sequence FDY (4B9; Hu4B9-65; Hu4B9-82, -83) and SEQ ID NO: 11 (4B9; Hu4B9-65; Hu4B9-82, -83). Throughout the specification a particular SEQ ID NO. is followed in parentheses by the antibody that was the origin of that sequence. For example, "SEQ ID NO: 47 (Hu4B9-82, -83)" means that SEQ ID NO: 47 comes from the humanized antibody 4B9 denoted Hu4B9-82, -83.

In some embodiments, the heavy chain variable region comprises a $CDR_{H1}$ comprising the amino acid sequence of SEQ ID NO: 5 or SEQ ID NO: 7 (4B9; Hu4B9-65; Hu4B9-82, -83), a $CDR_{H2}$ comprising the amino acid sequence of SEQ ID NO: 6 (4B9; Hu4B9-65), and a $CDR_{H3}$ comprising the amino acid sequence of SEQ ID NO: 11 (4B9; Hu4B9-65; Hu4B9-82, -83).

In some embodiments, the heavy chain variable region comprises a CDR$_{H1}$ comprising the amino acid sequence of SEQ ID NO: 5 (4B9; Hu4B9-65; Hu4B9-82, -83) or SEQ ID NO: 47 (Hu4B9-82, -83), a CDR$_{H2}$ comprising the amino acid sequence of SEQ ID NO: 38 (Hu4B9-82, -83), and a CDR$_{H3}$ comprising the amino acid sequence of SEQ ID NO: 11 (4B9; Hu4B9-65; Hu4B9-82, -83).

Preferably, the CDR$_{H1}$, CDR$_{H2}$, and CDR$_{H3}$ sequences are interposed between human or humanized immunoglobulin FRs. The antibody can be an intact antibody or an antigen-binding antibody fragment.

In other embodiments, the antibody comprises (a) an immunoglobulin light chain variable region comprising the structure CDR$_{L1}$-CDR$_{L2}$-CDR$_{L3}$, and (b) an immunoglobulin heavy chain variable region, wherein the IgG light chain variable region and the IgG heavy chain variable region together define a single binding site for binding human FGFR2. A CDR$_{L1}$ comprises an amino acid sequence selected from the group consisting of SEQ ID NO: 12 (4B9) and SEQ ID NO: 41 (Hu4B9-65; Hu4B9-82; Hu4B9-83); a CDR$_{L2}$ comprises an amino acid sequence selected from the group consisting of SEQ ID NO: 13 (4B9) and SEQ ID NO: 42 (Hu4B9-65; Hu4B9-82; Hu4B9-83); and a CDR$_{L3}$ comprises an amino acid sequence of SEQ ID NO: 14 (4B9; Hu4B9-65; Hu4B9-82; Hu4B9-83).

In some embodiments, the light chain variable region comprises a CDR$_{L1}$ comprising the amino acid sequence of SEQ ID NO: 12 (4B9); a CDR$_{L2}$ comprising the amino acid sequence of SEQ ID NO: 13 (4B9); and a CDR$_{L3}$ comprising the amino acid sequence of SEQ ID NO: 14 (4B9; Hu4B9-65; Hu4B9-82; Hu4B9-83).

In some embodiments, the light chain variable region comprises a CDR$_{L1}$ comprising the amino acid sequence of SEQ ID NO: 41 (Hu4B9-65; Hu4B9-82; Hu4B9-83); a CDR$_{L2}$ comprising the amino acid sequence of SEQ ID NO: 42 (Hu4B9-65; Hu4B9-82; Hu4B9-83); and a CDR$_{L3}$ comprising the amino acid sequence of SEQ ID NO: 14 (4B9; Hu4B9-65; Hu4B9-82; Hu4B9-83).

Preferably, the CDR$_{L1}$, CDR$_{L2}$, and CDR$_{L3}$ sequences are interposed between human or humanized immunoglobulin FRs. The antibody can be an intact antibody or an antigen-binding antibody fragment.

In some embodiments, the antibody comprises: (a) an immunoglobulin heavy chain variable region comprising the structure CDR$_{H1}$-CDR$_{H2}$-CDR$_{H3}$ and (b) an immunoglobulin light chain variable region comprising the structure CDR$_{L1}$-CDR$_{L2}$-CDR$_{L3}$, wherein the heavy chain variable region and the light chain variable region together define a single binding site for binding human FGFR2. The CDR$_{H1}$ is an amino acid sequence selected from the group consisting of SEQ ID NO: 5 or SEQ ID NO: 7 (4B9; Hu4B9-65; Hu4B9-82, -83); the CDR$_{H2}$ is an amino acid sequence selected from the group consisting of SEQ ID NO: 6 (4B9; Hu4B9-65) and SEQ ID NO: 38 (Hu4B9-82, -83); and the CDR$_{H3}$ is an amino acid sequence selected from the group consisting of amino acid sequence FDY and SEQ ID NO: 11 (4B9; Hu4B9-65; Hu4B9-82, -83). The CDR$_{L1}$ is an amino acid sequence selected from the group consisting of SEQ ID NO: 12 (4B9) and SEQ ID NO: 41 (Hu4B9-65; Hu4B9-82; Hu4B9-83); the CDR$_{L2}$ is an amino acid sequence selected from the group consisting of SEQ ID NO: 13 (4B9) and SEQ ID NO: 42 (Hu4B9-65; Hu4B9-82; Hu4B9-83); and the CDR$_{L3}$ comprises the amino acid sequence of SEQ ID NO: 14 (4B9; Hu4B9-65; Hu4B9-82; Hu4B9-83).

In another embodiment, the antibody comprises an immunoglobulin heavy chain variable region selected from the group consisting of SEQ ID NO: 2 (4B9), SEQ ID NO: 35 (Hu4B9-65), and SEQ ID NO: 37 (Hu4B9-82, -83), and an immunoglobulin light chain variable region selected from the group consisting of SEQ ID NO: 4 (4B9), SEQ ID NO: 40 (Hu4B9-65), SEQ ID NO: 44 (Hu4B9-82) and SEQ ID NO: 46 (Hu4B9-83).

In some embodiments, the antibody comprises an immunoglobulin heavy chain variable region comprising the amino acid sequence of SEQ ID NO: 2 (4B9), and an immunoglobulin light chain variable region comprising the amino acid sequence of SEQ ID NO: 4 (4B9).

In some embodiments, the antibody comprises an immunoglobulin heavy chain variable region comprising the amino acid sequence of SEQ ID NO: 35 (Hu4B9-65), and an immunoglobulin light chain variable region comprising the amino acid sequence of SEQ ID NO: 40 (Hu4B9-65).

In some embodiments, the antibody comprises an immunoglobulin heavy chain variable region comprising the amino acid sequence of SEQ ID NO: 37 (Hu4B9-82, -83), and an immunoglobulin light chain variable region comprising the amino acid sequence of SEQ ID NO: 44 (Hu4B9-82).

In some embodiments, the antibody comprises an immunoglobulin heavy chain variable region comprising the amino acid sequence of SEQ ID NO: 37 (Hu4B9-82, -83), and an immunoglobulin light chain variable region comprising the amino acid sequence of SEQ ID NO: 46 (Hu4B9-83).

In other embodiments, the antibody comprises (i) an immunoglobulin heavy chain selected from the group consisting of SEQ ID NO: 21 (4B9), SEQ ID NO: 54 (Hu4B9-65), and SEQ ID NO: 56 (Hu4B9-82, -83), and (ii) an immunoglobulin light chain selected from the group consisting of SEQ ID NO: 23 (4B9), SEQ ID NO: 58 (Hu4B9-65), SEQ ID NO: 60 (Hu4B9-82) and SEQ ID NO: 62 (Hu4B9-83).

In certain embodiments, the antibody comprises (i) an immunoglobulin heavy chain comprising the amino acid sequence of SEQ ID NO: 21 (4B9), and (ii) an immunoglobulin light chain comprising the amino acid sequence of SEQ ID NO: 23 (4B9).

In certain embodiments, the antibody comprises (i) an immunoglobulin heavy chain comprising the amino acid sequence of SEQ ID NO: 54 (Hu4B9-65), and (ii) an immunoglobulin light chain comprising the amino acid sequence of SEQ ID NO: 58 (Hu4B9-65).

In certain embodiments, the antibody comprises (i) an immunoglobulin heavy chain comprising the amino acid sequence of SEQ ID NO: 56 (Hu4B9-82, -83), and (ii) an immunoglobulin light chain comprising the amino acid sequence of SEQ ID NO: 60 (Hu4B9-82).

In certain embodiments, the antibody comprises (i) an immunoglobulin heavy chain comprising the amino acid sequence of SEQ ID NO: 56 (Hu4B9-82, -83), and (ii) an immunoglobulin light chain comprising the amino acid sequence of SEQ ID NO: 62 (Hu4B9-83).

In other embodiments, an isolated antibody that binds human FGFR2 comprises an immunoglobulin heavy chain variable region comprising an amino acid sequence that is at least 70%, 75%, 80%, 85%, 90%, 95%, 98%, or 99% identical to the entire variable region or the framework region sequence of SEQ ID NO: 2 (4B9), SEQ ID NO: 35 (Hu4B9-65), and SEQ ID NO: 37 (Hu4B9-82, -83).

In other embodiments, an isolated antibody that binds human FGFR2 comprises an immunoglobulin light chain variable region comprising an amino acid sequence that is at least 70%, 75%, 80%, 85%, 90%, 95%, 98%, or 99% identical to the entire variable region or the framework region sequence of SEQ ID NO: 4 (4B9), SEQ ID NO: 40 (Hu4B9-65), SEQ ID NO: 44 (Hu4B9-82) and SEQ ID NO: 46 (Hu4B9-83).

Homology or identity may be determined in various ways that are within the skill in the art, for instance, using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) PROC. NATL. ACAD. SCI. USA 87, 2264-2268; Altschul, (1993) J. MOL. EVOL. 36, 290-300; Altschul et al., (1997) NUCLEIC ACIDS RES. 25, 3389-3402, incorporated by reference) are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases see Altschul et al., (1994) NATURE GENETICS 6, 119-129 which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) PROC. NATL. ACAD. SCI. USA 89, 10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: −G, Cost to open gap [Integer]: default=5 for nucleotides/11 for proteins; −E, Cost to extend gap [Integer]: default=2 for nucleotides/1 for proteins; −q, Penalty for nucleotide mismatch [Integer]: default=−3; −r, reward for nucleotide match [Integer]: default=1; −e, expect value [Real]: default=10; −W, wordsize [Integer]: default=11 for nucleotides/28 for megablast/3 for proteins; −y, Dropoff (X) for blast extensions in bits: default=20 for blastn/7 for others; −X, X dropoff value for gapped alignment (in bits): default=15 for all programs, not applicable to blastn; and −Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gape Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In each of the foregoing embodiments, it is contemplated herein that immunoglobulin heavy chain variable region sequences and/or light chain variable region sequences that together bind human FGFR2 may contain amino acid alterations (e.g., at least 1, 2, 3, 4, 5, or 10 amino acid substitutions, deletions, or additions) in the framework regions of the heavy and/or light chain variable regions.

In some embodiments, an isolated antibody binds human FGFR2 with a $K_D$ of 5 nM, 4 nM, 3 nM, 2 nM, 1 nM, 950 pM, 900 pM, 850 pM, 800 pM, 750 pM, 700 pM, 650 pM, 600 pM, 550 pM, 500 pM, 450 pM, 400 pM, 350 pM, 300 pM, 250 pM, 200 pM, 150 pM, 100 pM, 50 pM or lower. Unless otherwise specified, $K_D$ values are determined by surface plasmon resonance methods under the conditions described, for example, in Examples 5 and 9.

Production of Antibodies

Methods for producing antibodies of the invention are known in the art. For example, DNA molecules encoding light chain variable regions and heavy chain variable regions can be chemically synthesized using the sequence information provided herein. Synthetic DNA molecules can be ligated to other appropriate nucleotide sequences, including, e.g., constant region coding sequences, and expression control sequences, to produce conventional gene expression constructs encoding the desired antibody. Production of defined gene constructs is within routine skill in the art. Alternatively, the sequences provided herein can be cloned out of hybridomas by conventional hybridization techniques or polymerase chain reaction (PCR) techniques, using synthetic nucleic acid probes whose sequences are based on sequence information provided herein, or prior art sequence information regarding genes encoding the heavy and light chains of murine antibodies in hybridoma cells.

Nucleic acids encoding desired antibodies can be incorporated (ligated) into expression vectors, which can be introduced into host cells through conventional transfection or transformation techniques. Exemplary host cells are E. coli cells, Chinese hamster ovary (CHO) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light or heavy chain variable regions.

Specific expression and purification conditions will vary depending upon the expression system employed. For example, if a gene is to be expressed in E. coli, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If the engineered gene is to be expressed in eukaryotic host cells, e.g., CHO cells, it is first inserted into an expression vector containing a suitable eukaryotic promoter, a secretion signal, IgG enhancers, and various introns. This expression vector optionally contains sequences encoding all or part of a constant region, enabling an entire, or a part of, a heavy or light chain to be expressed. The gene construct can be introduced into eukaryotic host cells using convention techniques. The host cells express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a moiety having another function (e.g., cytotoxicity). In some embodiments, a host cell is transfected with a single vector expressing a polypeptide expressing an entire, or part of, a heavy chain (e.g., a heavy chain variable region) or a light chain (e.g., a light chain variable region). In other embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain. In still other embodiments, a host cell is co-transfected with more than one expression vector (e.g., one expression vector expressing a polypeptide comprising an entire, or part of, a heavy chain or heavy chain variable region, and another expression vector expressing a polypeptide comprising an entire, or part of, a light chain or light chain variable region).

A polypeptide comprising an immunoglobulin heavy chain variable region or a light chain variable region can be produced by growing a host cell transfected with an expression vector encoding such variable region, under conditions that permit expression of the polypeptide. Following expression, the polypeptide can be harvested and purified using techniques well known in the art, e.g., affinity tags such as glutathione-S-transferase (GST) and histidine tags.

A monoclonal antibody that binds human FGFR2, or an antigen-binding fragment of the antibody, can be produced by growing a host cell transfected with: (a) an expression vector that encodes a complete or partial immunoglobulin heavy chain, and a separate expression vector that encodes a complete or partial light chain; or (b) a single expression vector that encodes both chains (e.g., complete or partial heavy and light chains) under conditions that permit expression of both chains. The intact antibody (or the antigen-binding fragment of the antibody) can be harvested and purified using techniques well known in the art, e.g., Protein A, Protein G, affinity tags such as glutathione-S-transferase (GST) and histidine tags. It is within ordinary skill in the art to express the heavy chain and the light chain from a single expression vector or from two separate expression vectors.

Modifications to the Antibodies

Methods for reducing or eliminating the antigenicity of antibodies and antibody fragments are known in the art. When the antibodies are to be administered to a human, the antibodies preferably are "humanized" to reduce or eliminate antigenicity in humans. Preferably, the humanized antibodies have the same, or substantially the same, affinity for the antigen as the non-humanized mouse antibody from which it was derived.

In one humanization approach, chimeric proteins are created in which mouse immunoglobulin constant regions are replaced with human immunoglobulin constant regions. See, e.g., Morrison et al., 1984, PROC. NAT. ACAD. SCI. 81:6851-6855, Neuberger et al., 1984, NATURE 312:604-608; U.S. Pat. Nos. 6,893,625 (Robinson); 5,500,362 (Robinson); and 4,816,567 (Cabilly).

In an approach known as CDR grafting, the CDRs of the light and heavy chain variable regions are grafted into frameworks from another species. For example, murine CDRs can be grafted into human FRs. In some embodiments of the invention, the CDRs of the light and heavy chain variable regions of an anti-FGFR2 antibody are grafted into human FRs or consensus human FRs. To create consensus human FRs, FRs from several human heavy chain or light chain amino acid sequences are aligned to identify a consensus amino acid sequence. CDR grafting is described in U.S. Pat. Nos. 7,022,500 (Queen); 6,982,321 (Winter); 6,180,370 (Queen); 6,054,297 (Carter); 5,693,762 (Queen); 5,859,205 (Adair); 5,693,761 (Queen); 5,565,332 (Hoogenboom); 5,585,089 (Queen); 5,530,101 (Queen); Jones et al. (1986) NATURE 321: 522-525; Riechmann et al. (1988) NATURE 332: 323-327; Verhoeyen et al. (1988) SCIENCE 239: 1534-1536; and Winter (1998) FEBS LETT 430: 92-94.

In an approach called "SUPERHUMANIZATION™," human CDR sequences are chosen from human germline genes, based on the structural similarity of the human CDRs to those of the mouse antibody to be humanized. See, e.g., U.S. Pat. No. 6,881,557 (Foote); and Tan et al., 2002, J. IMMUNOL 169:1119-1125.

Other methods to reduce immunogenicity include "reshaping," "hyperchimerization," and "veneering/resurfacing." See, e.g., Vaswami et al., 1998, ANNALS OF ALLERGY, ASTHMA, & IMMUNOL. 81:105; Roguska et al., 1996, PROT. ENGINEER 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, N.Y.), which involves a vaccinia virus-based vector to express antibodies in mammalian cells. High levels of combinatorial diversity of IgG heavy and light chains are said to be produced. See, e.g., U.S. Pat. Nos. 6,706,477 (Zauderer); 6,800,442 (Zauderer); and 6,872,518 (Zauderer).

Another approach for converting a mouse antibody into a form suitable for use in humans is technology practiced commercially by KaloBios Pharmaceuticals, Inc. (Palo Alto, Calif.). This technology involves the use of a proprietary human "acceptor" library to produce an "epitope focused" library for antibody selection.

Another approach for modifying a mouse antibody into a form suitable for medical use in humans is HUMAN ENGINEERING™ technology, which is practiced commercially by XOMA (US) LLC. See, e.g., PCT Publication No. WO 93/11794 and U.S. Pat. Nos. 5,766,886; 5,770,196; 5,821,123; and 5,869,619.

Any suitable approach, including any of the above approaches, can be used to reduce or eliminate human immunogenicity of an antibody disclosed herein.

If the antibody is for use as a therapeutic agent, it can be conjugated to an effector moiety such as a small molecule toxin or a radionuclide using standard in vitro conjugation chemistries. If the effector moiety is a polypeptide, the antibody can be chemically conjugated to the effector or joined to the effector as a fusion protein. Construction of fusion proteins is within ordinary skill in the art.

Use of Antibodies

Antibodies disclosed herein can be used to treat various forms of cancer, e.g., breast, ovarian, prostate, cervical, colorectal, lung, pancreatic, gastric, and head and neck cancers. The cancer cells are exposed to a therapeutically effective amount of the antibody so as to inhibit or reduce proliferation of the cancer cells. In some embodiments, the antibodies inhibit cancer cell proliferation by at least 40%, 50%, 60%, 70%, 80%, 90%, 95%, 98%, 99%, or 100%.

In some embodiments, the disclosed antibodies can be used in a method to inhibit tumor growth in a human patient. The method comprises administering to the patient a therapeutically effective amount of the antibody. Cancers associated with FGFR2 overexpression and/or activation include breast cancer, ovarian cancer, prostate cancer, cervical cancer, lung cancer, some forms of brain cancer, melanomas, and gastrointestinal cancers (e.g., colorectal, pancreatic, gastric, head and neck).

As used herein, "treating" a disease means: (a) reducing symptoms of the disease; (b) inhibiting progression of the disease; (c) causing regression of the disease; or (d) curing the disease.

Generally, a therapeutically effective amount of active component is in the range of 0.1 mg/kg to 100 mg/kg, e.g., 1 mg/kg to 100 mg/kg, 1 mg/kg to 10 mg/kg. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount and the disease being treated. Exemplary dosing frequencies are once per day, once per week and once every two weeks. A preferred route of administration is parenteral, e.g., intravenous infusion. Formulation of monoclonal antibody-based drugs is within ordinary skill in the art. In some embodiments of the invention a monoclonal antibody is lyophilized and reconstituted in buffered saline at the time of administration.

For therapeutic use, an antibody preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing antibodies of the invention can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. A preferred route of administration for monoclonal antibodies is IV infusion. Useful formulations can be prepared by methods well known in the pharmaceutical art. For example, see *Remington's Pharmaceutical Sciences*, 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

EXAMPLES

The following Examples are merely illustrative and are not intended to limit the scope or content of the invention in any way.

Example 1

Cell Lines and Reagents

KATO III, HEC-1-A, AN3 CA, SNU-16, and human lung cancer cell lines were acquired from the American Type Culture Collection (Rockville, Md.). FDCP-1 and Ba/F3, MFM-223, MFE-296, MFE-280, MFE-319 and ESS-1 cells were obtained from the German Collection of Microorganisms and Cell Cultures. All human cell lines were cultured according to the instructions specified by the suppliers, at 37° C., in an atmosphere containing 5% $CO_2$. All FGFs were purchased from R&D Systems, Inc. (Minneapolis, Minn.).

To establish cell-based assays to screen for functional FGFR2 antibodies, we first engineered Ba/F3 and FDCP-1 cells to express wild type FGFR2 and cancer-associated mutants or variants of FGFR2. FGFR-driven FDCP cells and Ba/F3 cells were obtained by the following methods. FDCP-1 cells were transfected by electroporation with plasmids encoding the IIIb, IIIc isoform or C-terminally truncated variant of human FGFR2 as well as cancer-associated FGFR2-IIIb S252W, or FGFR2-IIIb N550K mutants. Following selection with G418 (600 µg/ml), single clones were isolated and tested for their FGF1-dependent proliferation in the absence of IL3 by the MTT [3-(4,5-dimethylthiazol-2-yl)-2, 5-diphenyltetrazolium bromide] assay (Sigma-Aldrich, St. Louis, Mo.). MTT reagent (10 µl) was added to the cells and the reaction was stopped with 100 µl of 10% SDS with 2N HCL after four hours. The plates were analyzed the following day. The clones that exhibited robust FGF-1-dependent proliferation in the absence of IL3 were used for subsequent studies. To generate retroviruses expressing FGFR2, cDNAs encoding various human FGFR2 variants were each inserted into a retroviral vector. Retroviruses were produced by transfecting Phoenix cells using Lipofectamine 2000 (Invitrogen, Carlsbad, Calif.). Supernatants containing the retroviruses were used to infect Ba/F3 cells by centrifugation at 2500 rpm for 90 minutes, in the presence of 8 µg/ml of polybrene (Sigma-Aldrich). Individual clones were isolated by limiting dilution, and cell surface receptor expression was verified by flow cytometry.

Cancer cell lines with FGFR amplification were identified as follows. The CGP copy number database at the Wellcome Trust Sanger Institute (www.sanger.ac.uk) was queried for FGFR2 amplification (gene copy number >7). The copy number of the cell lines with potential FGFR2 amplification was analyzed by quantitative PCR (qPCR) using FGFR2 specific primers (5'-ACTTGGGCTGGAGTGATTTG-3' (SEQ ID NO: 24) and 5'-AATCCCATCTGCACACTTCC-3' (SEQ ID NO: 25)) and reference gene (transketolase) primers (5'-CAAAAACATGGCTGAGCAGA-3' (SEQ ID NO: 26) and 5'-GAAACAGGCCCCACTTTGTA-3' (SEQ ID NO: 27)). The FGFR2 gene copy number was calculated essentially as described in Toyokawa et al., 2009, ONCOL. REP. 21:875-880.

FGFR gene expression analysis was performed as follows. Total RNA was isolated by the RNeasy™ mini kit (Qiagen, Valencia, Calif.). Quantitative RT-PCR (qRT-PCR) was performed using a QuantiTect™ SYBR Green RT-PCR kit (Qiagen), with primers specific for FGFR2, FGFR2-IIIb, FGFR2-IIIc, and HPRT. The expression levels were normalized to HPRT.

Figure 2:
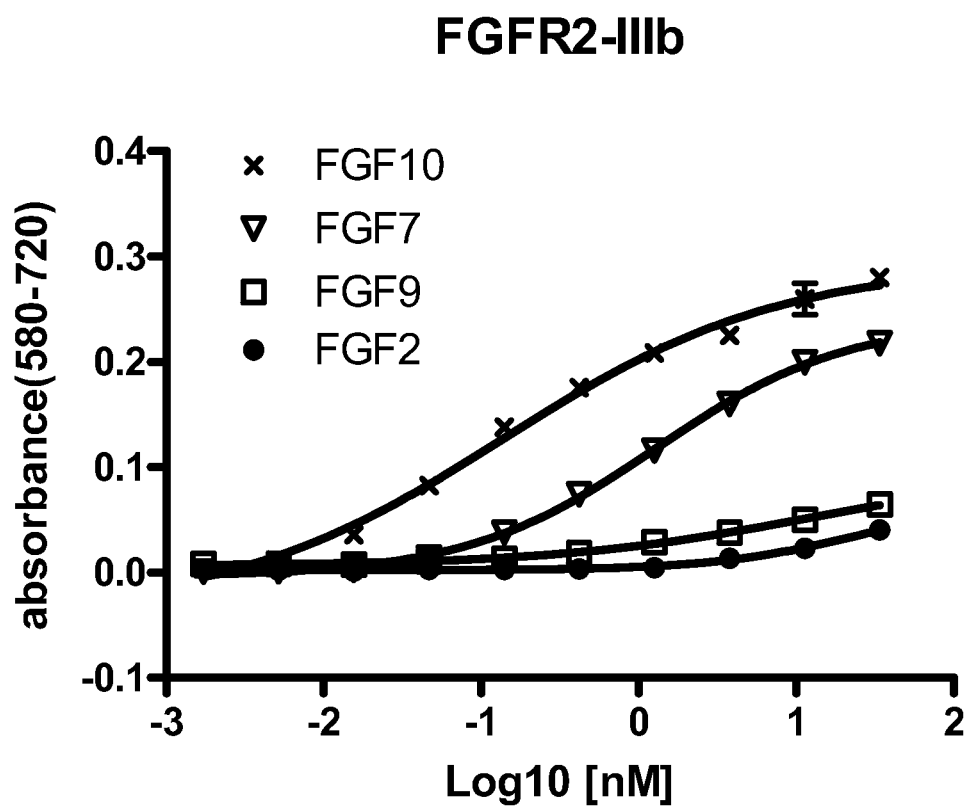
FIG. 2 is a graph summarizing results from an experiment to measure stimulation of proliferation of FGFR2-IIIb-expressing FDCP-1 cells by FGF2 (●), FGF7 (▽), FGF9 (□) and FGF10 (x).
Figure 3:
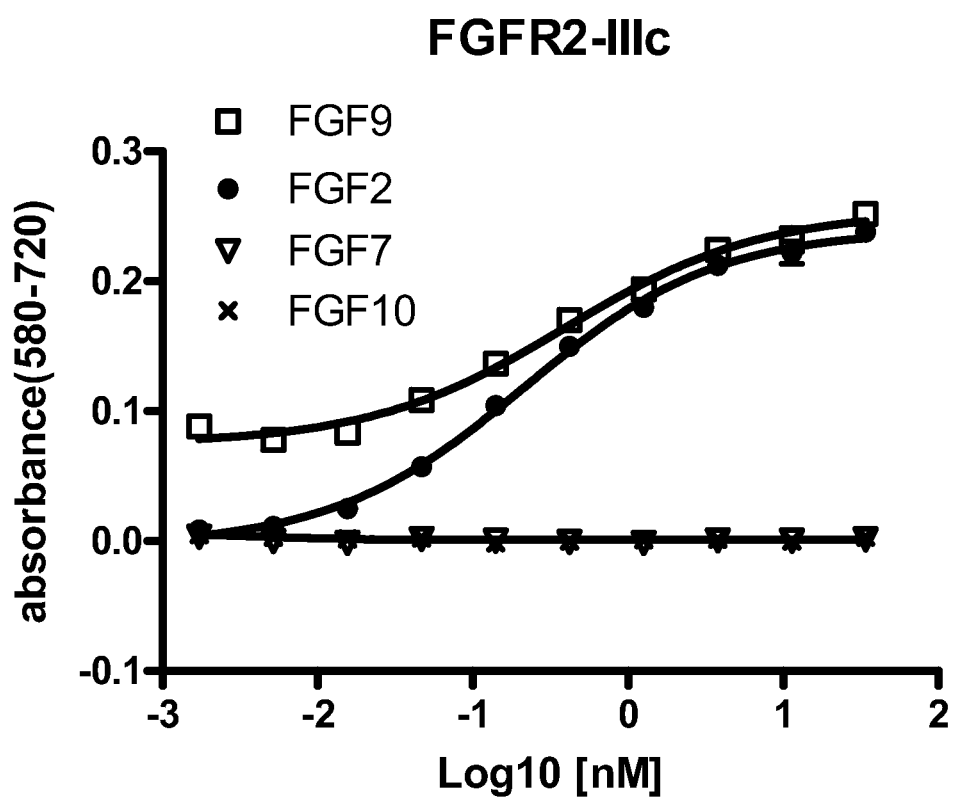
FIG. 3 is a graph summarizing results from an experiment to measure stimulation of proliferation of FGFR2-IIIc-expressing FDCP-1 cells by FGF2 (●), FGF7 (▽), FGF9 (□) and FGF10 (x).

Previous studies have demonstrated that ectopic expression of FGFRs in murine pro-B Ba/F3 or bone marrow FDCP-1 cells confers FGF1-dependent proliferation in the absence of IL-3 (Tannheimer et al., 2000, BREAST CANCER RES. 2:311-320; Ornitz et al., 1996, J. BIOL. CHEM. 271:15292-15297). As expected, there was no noticeable proliferation of FDCP-1 cells stably expressing wild-type FGFR2 in the absence of IL-3 and FGF1. It was known that FGF1, 3, 7, 10 and 22 transduce signals through FGFR2-IIIb, and that FGFR2-IIIc responds to a broader panel of ligands including FGF1, 2, 4, 6, 9, 16, 17, 18 and 20 (Tannheimer et al., supra; Ornitz et al., supra; Zhang et al., 2006, J. BIOL. CHEM. 281: 15964-15700). The proliferation of FDCP-1 cells expressing the IIIb isoform of FGFR2 was stimulated by FGF7 and FGF10, but not by FGF2 and FGF9 (FIG. 2). The proliferation of cells expressing the IIIc isoform was enhanced by FGF2 and FGF9 specifically (FIG. 3).

Example 2

Production of Anti-FGFR2 Monoclonal Antibodies

Mice were immunized with a 1:1 mixture of human FGFR2 IgD2-IgD3 (IIIb) and human FGFR2 IgD2-IgD3 (IIIc) fused with a human Fc moiety at their C-termini. Mouse immunizations and cell fusions were performed by a commercial vendor (Precision Antibody, Columbia, Md.).

In a primary screen, hybridoma supernatants were screened to detect binding to human FGFR2 IgD2-IgD3, using an ELISA format. Antibodies that passed the primary screen were subjected to a secondary screen, which was a cell-based proliferation assay described in Example 3 (below).

The primary screen was performed using the supernatants of the murine hybridoma clones yielded from the splenic fusion of the mice immunized with the extracellular domain of human FGFR2. Assay plates were coated with 100 ng/well of recombinant soluble FGFR2 extracellular domain and then blocked with 5% milk in PBS for one hour at room temperature. Then 50 μA of hybridoma supernatant was added to each well to allow antibody binding for one hour at room temperature. Plates were washed three times with wash buffer (PBS with 0.1% Tween 20) followed by incubation with a HRP-conjugated goat anti-mouse IgG heavy and light chain secondary antibody. The assay was developed using TMB (tetramethylbenzene) as a substrate, and absorbance was read at 620 nm.

Example 3

Identification of FGFR2 Antagonist Antibodies

To screen for FGFR2 antagonist antibodies, hybridoma supernatants containing FGFR2 antibodies were added to FDCP cells ectopically expressing one of the following five forms of FGFR2: (1) wild type FGFR2-IIIb; (2) wild type FGFR2-IIIc; (3) FGFR2-III(b) S252W; (4) FGFR2-III(b) N550K; and (5) FGFR2-III(b) with C-terminal truncation. The supernatants were added to the FGFR2-expressing cells at a 1:1 ratio (volume) in a flat-bottomed 96-well plate (70, 000 cells/well) with heparin (5 μg/ml)±FGF1 (8 ng/ml). After incubation at 37° C. for 2 days, MTT assays were conducted as described above.

The supernatant of clone 4B9 demonstrated potent and selective inhibition of the FDCP-1 proliferation driven by the IIIb-isoform of FGFR2. Antibody 4B9 (also referred to as antibody GP369), produced by clone 4B9, was purified by conventional techniques for further characterization. Surface plasmon resonance analysis indicated that antibody 4B9 exhibited strong affinity towards human FGFR2-IIIb and showed no detectable binding to the human FGFR2-IIIc. No binding of antibody 4B9 to human FGFR1-IIIc or FGFR3-IIIb was detected.

Example 4

Sequence Analysis

The light chain isotype and heavy chain isotype of antibody 4B9 in Example 1 was determined using the IsoStrip™ Mouse Monoclonal Antibody Isotyping Kit according to the manufacturer's instructions (Roche Applied Science, Indianapolis, Ind.). The antibody was determined to be Kappa light chain and IgG1 heavy chain.

The heavy and light chain variable regions of antibody 4B9 were sequenced using 5' RACE (Rapid Amplification of cDNA Ends). Total RNA was extracted from the 4B9 monoclonal hybridoma cell line using the RNeasy™ Miniprep kit according to the vendor's instructions (Qiagen, Valencia, Calif.). Full-length first strand cDNA containing 5' ends was generated using SMARTer™ RACE cDNA Amplification Kit (Clontech, Palo Alto, Calif.) according to the manufacturer's instructions using random primers for 5' RACE.

The variable regions of the kappa and heavy IgG1 chains were amplified by PCR, using KOD Hot Start™ Polymerase (EMD Chemicals, Gibbstown, N.J.) according to the manufacturer's instructions. For amplification of 5' cDNA ends in conjunction with the SMARTer™ RACE cDNA Amplification Kit, the Universal Primer Mix A primer (Clontech), a mix of 5'CTAATACGACTCACTATAGGGCAAG-CAGTGGTATCAACGCAGAGT 3' (SEQ ID NO: 28) and 5' CTAATACGACTCACTATAGGGC 3' (SEQ ID NO: 29), was used as a 5' primer. The heavy chain variable region was amplified using the above 5' primers and a 3' IgG 1 constant region specific primer, 5' TATGCAAGGCTTACAACCACA 3' (SEQ ID NO: 30). The kappa chain variable region was amplified with the above 5' primers and a 3' kappa constant region specific primer, CGACTGAGGCACCTCCAGAT-GTT 3' (SEQ ID NO: 31).

Individual PCR products were isolated by agarose gel electrophoresis and purified using the Qiaquick™ Gel Purification kit according to the manufacturer's instructions (Qiagen). The PCR products were subsequently cloned into the pCR4Blunt plasmid using the Zero Blunt TOPO® PCR Cloning Kit according to the manufacturer's instructions (Invitrogen) and transformed into DH5-α bacteria (Invitrogen) through standard molecular biology techniques. Plasmid DNA isolated from transformed bacterial clones was sequenced using M13 Forward (5' GTAAAACGACGGC-CAGT 3') (SEQ ID NO: 32) and M13 Reverse primers (5' CAGGAAACAGCTATGACC 3') (SEQ ID NO: 33) by Beckman Genomics (Danvers, Mass.), using standard dideoxy DNA sequencing methods to identify the sequence of the variable region sequences. The sequences were analyzed using Vector NTI software (Invitrogen) and the IMGT/V-Quest web server to identify and confirm variable region sequences.

The nucleic acid sequences encoding and the protein sequences defining variable regions of antibody 4B9 are summarized below (amino terminal signal peptide sequences are not shown). CDR sequences (Kabat definition) are shown in bold/underlined in the amino acid sequences.

```
Nucleic Acid Sequence Encoding the Heavy Chain Variable Region of
Antibody 4B9
                                                             (SEQ ID NO: 1)
   1 gaggttcagc tccagcagtc tgggactgtg ctggcaaggc ctggggcttc agtgaagatg
  61 tcctgcaaga cttctggcta cacatttacc agctactgga tgcactgggt aaaacagagg
 121 cctggacagg gtctggaatg gatagggct atttatcctg gaaatagtga tactgactac
 181 agccagaagt tcaagggcaa ggccacactg actgcagtca catccgccac cactgcctac
 241 atggaactca gcagcctgac aaatgaggac tctgcggtct attactgttc aaagtttgac
 301 tactggggcc aagcaccac tctcacagtc tcctca Protein Sequence Defining the Heavy Chain Variable Region of
Antibody 4B9
                                                             (SEQ ID NO: 2)
   1 evqlqqsgtv larpgasvkm scktsgytft sywmhwvkqr pgqglewiga iypgnsdtdy
  61 sqkfkgkatl tavtsattay melssltned savyycskfd ywgqgttltv ss Nucleic Acid Sequence Encoding the Kappa Chain Variable Region of
Antibody 4B9
                                                             (SEQ ID NO: 3)
   1 caaattgttc tcacccagtc tccagcactc atgtctgcat ctccagggga gaaggtcacc
  61 atgacctgca gtgccagctc aagtgtaaat tacatgtact ggtaccagca gaagccaaga
 121 tcctccccca aaccctggat ttatctcaca tccaacctgg cttctggagt ccctgctcgc
 181 ttcagtggca ggggtctgg gacctcttac tctctcacaa tcagcagcat ggaggctgaa
 241 gatgctgcca cttattactg ccagcagtgg agtagtaacc cgtacacgtt cggagggggg
 301 accaagctgg aaataaaa Protein Sequence Defining the Kappa Chain Variable Region of
Antibody 4B9
                                                             (SEQ ID NO: 4)
   1 qivltqspal msaspgekvt mtcsasssvn ymywyqqkpr sspkpwiylt snlasgvpar
  61 fsgrgsgtsy sltissmeae daatyycqqw ssnpytfggg tkleik
```

Table 1 is a concordance chart showing the SEQ ID NO. of each sequence discussed in this Example.

TABLE 1

| SEQ. ID NO. | Antibody 4B9 Nucleic Acid or Protein |
| --- | --- |
| 1 | Heavy Chain Variable Region—nucleic acid |
| 2 | Heavy Chain Variable Region—protein |
| 3 | Light (kappa) Chain Variable Region—nucleic acid |
| 4 | Light (kappa) Chain Variable Region—protein |
| 5 | Heavy Chain CDR$_1$ (Kabat definition) |
| 6 | Heavy Chain CDR$_2$ (Kabat definition) |
| 11 | Heavy Chain CDR$_3$ (IGMT definition) |
| 12 | Light (kappa) Chain CDR$_1$ (Kabat definition) |
| 13 | Light (kappa) Chain CDR$_2$ (Kabat definition) |
| 14 | Light (kappa) Chain CDR$_3$ (Kabat definition) |

Mouse monoclonal antibody heavy chain CDR sequences (Kabat, Chothia, and IMGT definitions) are shown in Table 2.

TABLE 2

| | CDR1 | CDR2 | CDR3 |
| --- | --- | --- | --- |
| | | Kabat | |
| 4B9 | SYWMH (SEQ ID NO: 5) | AIYPGNSDTDYSQ KFKG (SEQ ID NO: 6) | FDY |
| | | Chothia | |
| 4B9 | GYTFTSY (SEQ ID NO: 7) | YPGNSD (SEQ ID NO: 8) | FDY |
| | | IMGT | |
| 4B9 | GYTFTSYW (SEQ ID NO: 9) | IYPGNSDT (SEQ ID NO: 10) | SKFDY (SEQ ID NO: 11) |

Mouse monoclonal antibody Kappa light chain CDR sequences (Kabat, Chothia, and IMGT definitions) are shown in Table 3.

TABLE 3

| | CDR1 | CDR2 | CDR3 |
| --- | --- | --- | --- |
| | | Kabat/Chothia | |
| 4B9 | SASSSVNYMY (SEQ ID NO: 12) | LTSNLAS (SEQ ID NO: 13) | QQWSSNPYT (SEQ ID NO: 14) |
| | | IMT | |
| 4B9 | SSVNY (SEQ ID NO: 15) | LTS | QQWSSNPYT (SEQ ID NO: 14) |

To create the complete heavy or kappa chain antibody sequences, each variable sequence above is combined with its respective constant region. For example, a complete heavy chain comprises the heavy variable sequence followed by the murine IgG1 heavy chain constant sequence and the complete kappa chain comprises a kappa variable sequence followed by the murine kappa light chain constant sequence.

Nucleic Acid Sequence Encoding the Murine IgG1 Heavy Chain
Constant Region (SEQ ID NO: 16)

```
  1 gccaaaacga cacccccatc tgtctatcca ctggcccctg gatctgctgc ccaaactaac
 61 tccatggtga ccctgggatg cctggtcaag ggctatttcc ctgagccagt gacagtgacc
121 tggaactctg gatccctgtc cagcggtgtg cacaccttcc cagctgtcct gcagtctgac
181 ctctacactc tgagcagctc agtgactgtc cctccagca cctggcccag ccagaccgtc
241 acctgcaacg ttgcccaccc ggccagcagc accaaggtgg acaagaaaat tgtgcccagg
301 gattgtggtt gtaagccttg catatgtaca gtcccagaag tatcatctgt cttcatcttc
361 cccccaaagc ccaaggatgt gctcaccatt actctgactc ctaaggtcac gtgtgttgtg
421 gtagacatca gcaaggatga tcccgaggtc cagttcagct ggtttgtaga tgatgtggag
481 gtgcacacag ctcagacgca accccgggag gagcagttca acagcacttt ccgctcagtc
541 agtgaacttc ccatcatgca ccaggactgg ctcaatggca aggagttcaa atgcagggtc
601 aacagtgcag cttttcctgc ccccatcgag aaaaccatct ccaaaaccaa aggcagaccg
661 aaggctccac aggtgtacac cattccacct cccaaggagc agatggccaa ggataaagtc
721 agtctgacct gcatgataac agacttcttc cctgaagaca ttactgtgga gtggcagtgg
781 aatgggcagc cagcggagaa ctacaagaac actcagccca tcatggacac agatggctct
841 tacttcgtct acagcaagct caatgtgcag aagagcaact gggaggcagg aaatactttc
901 acctgctctg tgttacatga gggcctgcac aaccaccata ctgagaagag cctctcccac
961 tctcctggta aa
```

Protein Sequence Defining the Murine IgG1 Heavy Chain Constant
Region (SEQ ID NO: 17)

```
  1 akttppsvyp lapgsaaqtn smvtlgclvk gyfpepvtvt wnsgslssgv htfpavlqsd
 61 lytlsssvtv psstwpsqtv tcnvahpass tkvdkkivpr dcgckpcict vpevssvfif
121 ppkpkdvlti tltpkvtcvv vdiskddpev qfswfvddve vhtaqtqpre eqfnstfrsv
181 selpimhqdw lngkefkcrv nsaafpapie ktisktkgrp kapqvytipp pkeqmakdkv
241 sltcmitdff peditvewqw ngqpaenykn tqpimdtdgs yfvysklnvq ksnweagntf
301 tcsvlheglh nhhtekslsh spgk
```

Nucleic Acid Sequence Encoding the Murine Kappa Light Chain Constant
Region (SEQ ID NO: 18)

```
  1 cgggctgatg ctgcaccaac tgtatccatc ttcccaccat ccagtgagca gttaacatct
 61 ggaggtgcct cagtcgtgtg cttcttgaac aacttctacc ccagagacat caatgtcaag
121 tggaagattg atggcagtga acgacaaaat ggtgtcctga cagttggac tgatcaggac
181 agcaaagaca gcacctacag catgagcagc accctcacat tgaccaagga cgagtatgaa
241 cgacataaca gctatacctg tgaggccact cacaagacat caacttcacc cattgtcaag
301 agcttcaaca ggaatgagtg t
```

Protein Sequence Defining the Murine Kappa Light Chain Constant
Region (SEQ ID NO: 19)

```
  1 radaaptvsi fppsseqlts ggasvvcfln nfyprdinvk wkidgserqn gvlnswtdqd
 61 skdstysmss tltltkdeye rhnsytceat hktstspivk sfnrnec
```

The following sequences represent the actual or comtemplated full length heavy and light chain sequences (i.e., containing both the variable and constant regions sequences) for each antibody described in this Example. Signal sequences for proper secretion of the antibodies are also included at the 5' end of the DNA sequences or the amino terminal end of the protein sequences. The variable region sequences can be ligated to other constant region sequences, to produce active full length IgG heavy and light chains.

Nucleic Acid Sequence Encoding the Full Length Heavy Chain Sequence
(Heavy Chain Variable Region and IgG1 Constant Region) of 4B9

(SEQ ID NO: 20)

```
   1 atggaatgta actggatact tcctttatt ctgtcggtaa cttcaggggt ctactcagag
  61 gttcagctcc agcagtctgg gactgtgctg gcaaggcctg gggcttcagt gaagatgtcc
 121 tgcaagactt ctggctacac atttaccagc tactggatgc actgggtaaa acagaggcct
 181 ggacagggtc tggaatggat aggggctatt tatcctggaa atagtgatac tgactacagc
 241 cagaagttca agggcaaggc cacactgact gcagtcacat ccgccaccac tgcctacatg
 301 gaactcagca gcctgacaaa tgaggactct gcggtctatt actgttcaaa gtttgactac
 361 tggggccaag gcaccactct cacagtctcc tcagccaaaa cgacaccccc atctgtctat
 421 ccactggccc ctggatctgc tgcccaaact aactccatgg tgaccctggg atgcctggtc
 481 aagggctatt tccctgagcc agtgacagtg acctggaact ctggatccct gtccagcggt
 541 gtgcacacct tcccagctgt cctgcagtct gacctctaca ctctgagcag ctcagtgact
 601 gtccctcca gcacctggcc cagccagacc gtcacctgca acgttgccca cccggccagc
 661 agcaccaagg tggacaagaa aattgtgccc agggattgtg gttgtaagcc ttgcatatgt
 721 acagtcccag aagtatcatc tgtcttcatc ttccccccaa agcccaagga tgtgctcacc
 781 attactctga ctcctaaggt cacgtgtgtt gtggtagaca tcagcaagga tgatcccgag
 841 gtccagttca gctggtttgt agatgatgtg gaggtgcaca gctcagac gcaacccgg
 901 gaggagcagt tcaacagcac tttccgctca gtcagtgaac ttcccatcat gcaccaggac
 961 tggctcaatg gcaaggagtt caaatgcagg gtcaacagtg cagcttttcc tgcccccatc
1021 gagaaaacca tctccaaaac caaaggcaga ccgaaggctc cacaggtgta caccattcca
1081 cctcccaagg agcagatggc caaggataaa gtcagtctga cctgcatgat aacagacttc
```

-continued
```
1141 ttccctgaag acattactgt ggagtggcag tggaatgggc agccagcgga gaactacaag
1201 aacactcagc ccatcatgga cacagatggc tctttacttcg tctacagcaa gctcaatgtg
1261 cagaagagca actgggaggc aggaaatact ttcacctgct ctgtgttaca tgagggcctg
1321 cacaaccacc atactgagaa gagcctctcc cactctcctg gtaaa
```

Protein Sequence Defining the Full Length Heavy Chain Sequence
(Heavy Chain Variable Region and IgG1 Constant Region) of 4B9
(SEQ ID NO: 21)
```
  1 mecnwilpfi lsvtsgvyse vqlqqsgtvl arpgasvkms cktsgytfts ywmhwvkqrp
 61 gqglewigai ypgnsdtdys qkfkgkatlt avtsattaym elssltneds avyycskfdy
121 wgqgttltvs sakttppsvy plapgsaaqt nsmvtlgclv kgyfpepvtv twnsgslssg
181 vhtfpavlqs dlytlsssvt vpsstwpsqt vtcnvahpas stkvdkkivp rdcgckpcic
241 tvpevssvfi fppkpkdvlt itltpkvtcv vvdiskddpe vqfswfvddv evhtaqtqpr
301 eeqfnstfrs vselpimhqd wlngkefkcr vnsaafpapi ektisktkgr pkapqvytip
361 ppkeqmakdk vsltcmitdf fpeditvewq wngqpaenyk ntqpimdtdg syfvysklnv
421 qksnweagnt ftcsvlhegl hnhhteksls hspgk
```

Nucleic Acid Sequence Encoding the Full Length Light Chain Sequence
(Kappa Chain Variable Region and Constant Region) of 4B9
(SEQ ID NO: 22)
```
  1 atggattttc aagtgcagat tttcagcttc ctgctaatga gtgcctcagt cataatgtcc
 61 aggggacaaa ttgttctcac ccagtctcca gcactcatgt ctgcatctcc aggggagaag
121 gtcaccatga cctgcagtgc cagctcaagt gtaaattaca tgtactggta ccagcagaag
181 ccaagatcct cccccaaacc ctggatttat ctcacatcca acctggcttc tggagtccct
241 gctcgcttca gtggcagggg gtctgggacc tcttactctc tcacaatcag cagcatggag
301 gctgaagatg ctgccactta ttactgccag cagtggagta gtaacccgta cacgttcgga
361 gggggaccaa agctggaaat aaaacgggct gatgctgcac caactgtatc catcttccca
421 ccatccagtg agcagttaac atctggaggt gcctcagtcg tgtgcttctt gaacaacttc
481 taccccagag acatcaatgt caagtggaag attgatggca gtgaacgaca aaatggtgtc
541 ctgaacagtt ggactgatca ggacagcaaa gacagcacct acagcatgag cagcaccctc
601 acattgacca aggacgagta tgaacgacat aacagctata cctgtgaggc cactcacaag
661 acatcaactt cacccattgt caagagcttc aacaggaatg agtgt
```

Protein Sequence Defining the Full Length Light Chain Sequence
(Kappa Chain Variable Region and Constant Region) of 4B9
(SEQ ID NO: 23)
```
  1 mdfqvqifsf llmsasvims rgqivltqsp almsaspgek vtmtcsasss vnymywyqqk
 61 prsspkpwiy ltsnlasgvp arfsgrgsgt sysltissme aedaatyycq qwssnpytfg
121 ggtkleikra daaptvsifp psseqltsgg asvvcflnnf yprdinvkwk idgserqngv
181 lnswtdqdsk dstysmsstl tltkdeyerh nsytceathk tstspivksf nrnec
```

Table 4 shows the correspondence between the full length sequences of the antibodies discussed in this Example with those presented in the Sequence Listing.

TABLE 4

| SEQ ID NO. | Antibody 4B9 Nucleic Acid or Protein |
|---|---|
| 20 | Heavy Variable + IgG1 Constant—nucleic acid |
| 21 | Heavy Variable + IgG1 Constant—protein |
| 22 | Kappa Variable + Constant—nucleic acid |
| 23 | Kappa Variable + Constant—protein |

Example 5

Binding Affinities

The binding affinities and binding kinetics of monoclonal antibody 4B9 were measured with respect to the following proteins (R&D Systems, Inc., Minneapolis, Minn.): recombinant human FGFR1 beta (IIIb)/Fc Chimera (rhFGFR1β-IIIc-Fc), recombinant human FGFR2 beta (IIIb)/Fc Chimera (rhFGFR2β-IIIb-Fc), recombinant human FGFR2 beta (IIIc)/Fc Chimera (rhFGFR2β-IIIc-Fc), recombinant human FGFR3 beta (IIIb)/Fc Chimera (rhFGFR3β-IIIb-Fc), and a version of recombinant human FGFR2 beta (IIIb)/Fc (in which the Fc region was removed enzymatically). Binding affinities and binding kinetics were measured by surface plasmon resonance using a Biacore T100 instrument (GE Healthcare, Piscataway, N.J.).

Rabbit anti-mouse IgGs (GE Healthcare) were immobilized on carboxymethylated dextran CM4 sensor chips (GE Healthcare) by amine coupling, using a standard coupling protocol, according to the vendor's instructions (GE Healthcare). The analyses were performed at 25° C. and 37° C., using PBS containing 0.05% surfactant P20 (GE Healthcare) as running buffer.

The antibodies were captured in individual flow cells at a flow rate of 10 λl/min. Injection time was varied for each antibody to yield an Rmax between 30 and 60 RU. Buffer and FGFR proteins diluted in running buffer were injected sequentially over a reference surface (no antibody captured) and the active surface (antibody to be tested) for 240 seconds at 60 μl/min. The dissociation phase was monitored for up to 900 seconds. The surface was then regenerated with two 60-second injections of 10 mM Glycine-HCl (pH 1.7), at a flow rate of 60 μl/minute. The FGFR protein concentration range tested was 50 to 3.125 nM (two-fold dilutions).

Kinetic parameters were determined using the kinetic function of the BIAevalutation software (GE Healthcare) with double reference subtraction. Kinetic parameters for each antibody, $k_a$ (association rate constant), $k_d$ (dissociation rate constant) and $K_D$ (equilibrium dissociation constant) were determined. Kinetic values of the monoclonal antibodies on FGFR proteins at 25° C. and 37° C. are summarized in Table 5.

TABLE 5

| Antibody | Target | Temp (° C.) | $k_a$ (M$^{-1}$s$^{-1}$) | $k_d$ (s$^{-1}$) | $K_D$ (M) |
|---|---|---|---|---|---|
| 4B9 | rhFGFR1β-IIIb-Fc | 25 | no binding | no binding | no binding |
| 4B9 | rhFGFR2β-IIIb-Fc | 25 | 9.4E+04 | 4.6E−05 | 6.1E−10 |

TABLE 5-continued

| Antibody | Target | Temp (° C.) | $k_a$ ($M^{-1}s^{-1}$) | $k_d$ ($s^{-1}$) | $K_D$ (M) |
|---|---|---|---|---|---|
| 4B9 | rhFGFR2β-IIIb-Fc | 37 | 3.44E+04 | 3.16E−05 | 2.96E−09 |
| 4B9 | rhFGFR2β-IIIb-cleaved | 25 | 5.5E+04 | 8.1E−05 | 4.2E−09 |
| 4B9 | rhFGFR2β-IIIb-cleaved | 37 | 2.54E+05 | 2.23E−04 | 1.20E−09 |
| 4B9 | rhFGFR2β-IIIc-Fc | 25 | no binding | no binding | no binding |
| 4B9 | rhFGFR3β-IIIb-Fc | 25 | no binding | no binding | no binding |

The results in Table 5 demonstrate that antibody 4B9 binds rhFGFR2β-IIIb with a $K_D$ of about 5 nM, 4 nM, 3 nM, 2 nM, 1 nM, 750 pM, 650 pM, 610 pM or less. The results also demonstrate that antibody 4B9 does not bind rhFGFR1β-IIIb, rhFGFR2β-IIIc, and rhFGFR3β-IIIb.

Example 6

Anti-Proliferative Activity

To assess the potency of antibody 4B9 quantitatively, we carried out dose-response studies, using FDCP-1 cells expressing FGFR2-IIIb or FGFR2-IIIc. FDCP-1 cells expressing FGFR2-IIIb or FGFR2-IIIc were seeded in a 96-well plate in the absence of IL3. Varied amounts of FGFs and heparin were added. MTT assays were carried out after 2-3 days. Varied amounts of antibody 4B9-containing supernatants were added to FDCP-1 cells expressing FGFR2-IIIb, FGFR2-IIIc, or C-terminally truncated FGFR2-IIIb, in the presence of FGF1 and heparin. MTT assays were carried out after 2 days. Varied amounts of purified antibody 4B9 were added to FDCP-1 cells expressing FGFR2-IIIb S252W or FGFR2-IIIb N550K in the presence of FGF1 and heparin. MTT assays were carried out after 2 days.

Figure 4:
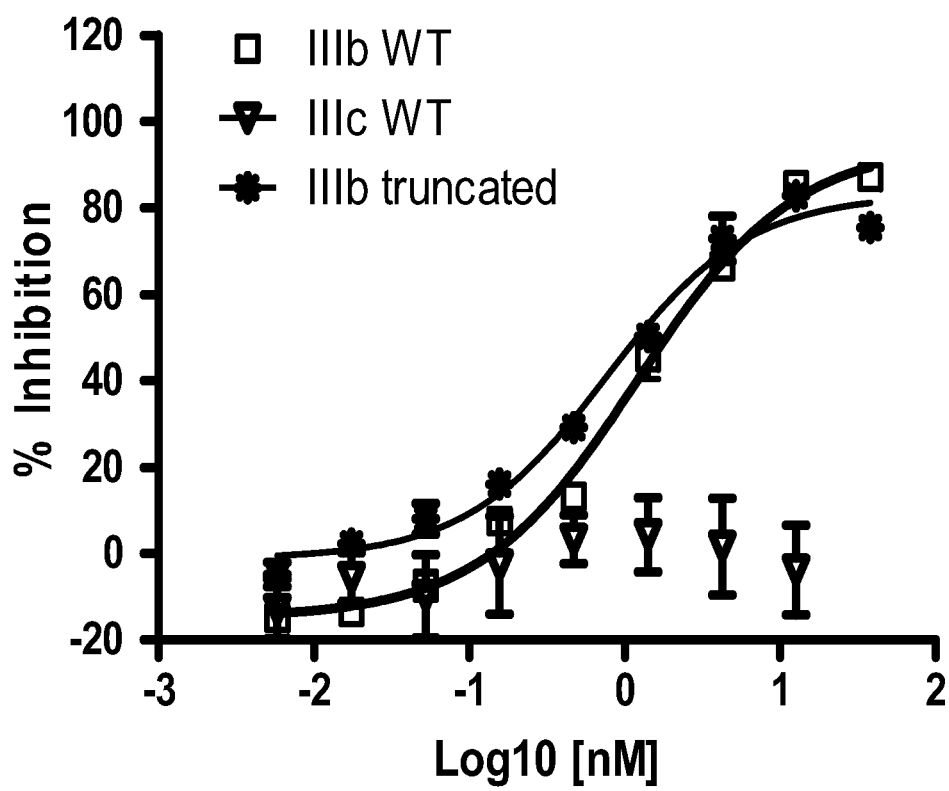
FIG. 4 is a graph summarizing results from an experiment to measure inhibition of proliferation of FDCP-1 cells expressing wild type FGFR2-IIIb (□), wild type FGFR2-IIIc (▽), or truncated FGFR2-IIIb (*), by treatment with antibody 4B9.

Antibody 4B9 potently inhibited FGF1-induced proliferation of FDCP-1 cells driven by FGFR2-IIIb, in a dose-dependent manner, while 4B9 had no significant effect on the FGF1-induced proliferation of FDCP cells expressing the FGFR2-IIIc (FIG. 4). C-terminally truncated FGFR2-IIIb, which causes constitutive phosphorylation of FRS2 adaptor molecule and activation of downstream signaling, is found in gastric and breast cancer cell lines (Itoh et al., 1994, CANCER RES. 54:3237-3241; Moffa et al., 2004, MOL. CANCER RES. 2:643-652). Antibody 4B9 potently inhibited the proliferation of FDCP-1 cells driven by the C-terminally truncated FGFR2-IIIb (FIG. 4).

Figure 5:
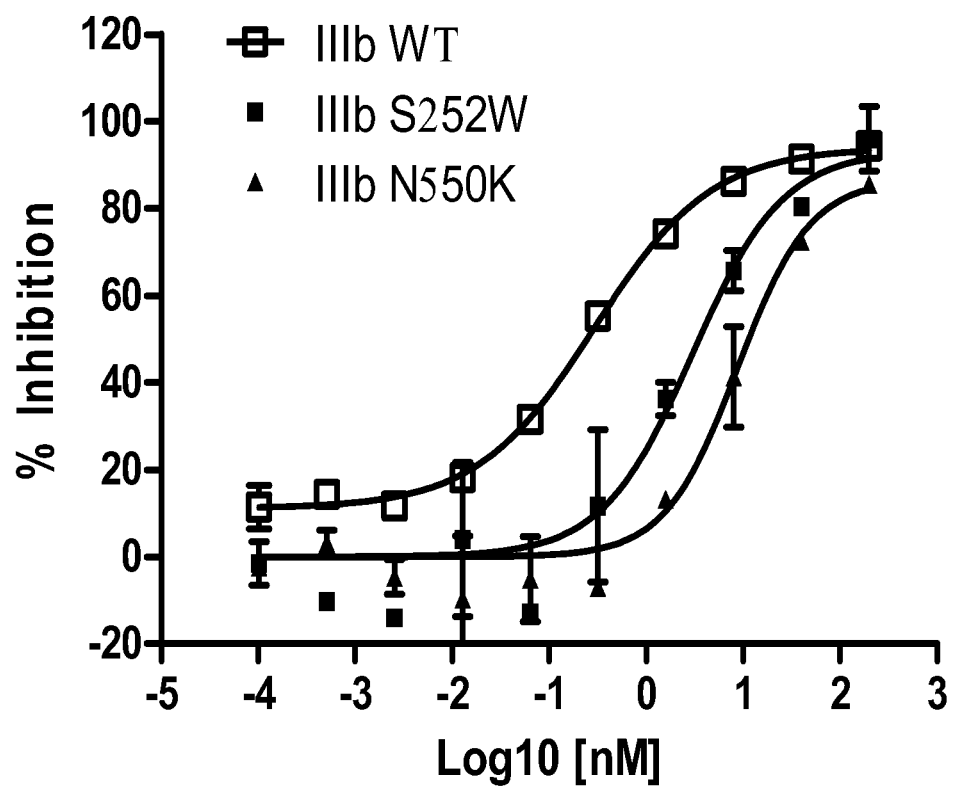
FIG. 5 is a graph summarizing results from an experiment to measure inhibition of proliferation of FDCP-1 cells expressing wild type FGFR2-IIIb (□), FGFR2-IIIb S252W (■), or FGFR2-IIIb N550K (▲), by treatment with antibody 4B9.

FGFR2 mutations have been reported in approximately 12% of endometrial tumor sample (Pollock et al., supra; Dutt et al., supra). Somatic activating mutations in FGFR2 cluster within the linker region between IgD2 and IgD3, the extracellular juxtamembrane domain, or the kinase domain. Two of the most common mutations in endometrial tumors are the S252W mutation (which alters ligand specificity and increases affinity of ligand binding) and the N550K mutation in the kinase domain (which enhances kinase activity). Purified antibody 4B9 potently inhibited cell proliferation driven by the wild type FGFR2-IIIb, as well as FGFR2-IIIb S252W and FGFR2-IIIb N550K, with $IC_{50}$ values of 0.3 nM, 3.0 nM and 8.1 nM, respectively (FIG. 5).

Example 7

Inhibition of FGFR2—Activated Signaling Pathways

We investigated the effect of antibody 4B9 on FGFR2-activated signaling pathways. To examine the effect of antibody 4B9 on tyrosine phosphorylation of FGFR2, SNU-16 cells were treated with antibodies at a dose of 5 μg/ml for 1 hour at 37° C., followed by stimulation with heparin alone (20 μg/ml) or heparin-plus-FGF7 (30 ng/ml) for 15 minutes. The cells were lysed in NP-40 lysis buffer containing 1% NP-40, 20 mM Tris-HCl (pH 8.0), 137 mM NaCl, 10% glycerol, 2 mM EDTA and supplemented with protease inhibitors (Roche Applied Science) and Halt phosphatase inhibitors (Thermo Scientific).

The lysates were analyzed by Western blot with anti-FGFR (Y653/Y654) (R&D Systems, Inc., Minneapolis, Minn.), anti-FGFR2 (sc-122) (Santa Cruz Biotechnology, Santa Cruz, Calif.), anti-phospho-ERK1/2 and anti-ERK1/2 (Cell Signaling Technology, Danvers, Mass.), anti-β-tubulin, clone AA2 (Millipore Corporation; Billerica, Mass.) antibodies. The immunoblots were detected by chemiluminescent substrate (ECL Plus™, Amersham Pharmacia Biotech, Piscataway, N.J.). Human Phospho-RTK and MAPK kinase arrays (R&D systems) were carried out according to manufacturer's instructions (R&D systems). For phospho-RTK arrays, the cells were lysed in NP-40 lysis buffer. The arrays were blocked in Array Buffer 1 at room temperature for one hour prior to the addition of cell lysates diluted in Array Buffer 1 and were then incubated at 4° C. overnight. The arrays were visualized by chemiluminescence. For phospho-MAPK arrays, the cells were lysed in Lysis Buffer 6. The diluted cell lysates were added to arrays. After incubation at 4° C. overnight, the arrays were mixed with anti-phospho-MAPK antibody for two hours at room temperature and visualized as described above.

FGF7 induced tyrosine phosphorylation of FGFR2 and subsequent activation of extracellular signal-regulated kinase 1 and 2 (ERK1/2) in Ba/F3 cells overexpressing FGFR2, and in FGFR2-amplified SNU-16 cells. Antibody 4B9 effectively suppressed the ligand-induced tyrosine phosphorylation of FGFR2 and activation of ERK1/2 in these cells. In addition, antibody 4B9 downregulated the FGFR2 protein level in SNU-16 cells. A slight decrease in the FGFR2 protein level was observed as early as two hours after exposure to the antibody. A dramatic reduction in the protein level was seen at the six-hour time point.

We investigated activation of downstream signaling pathways in these cell lines, using a phospho-MAPK array, which measures phosphorylation of ERKs, c-Jun $NH_2$-Terminal Kinases (JNKs), p38 MAPKs, AKTs, and their downstream effector molecules. We found little phosphorylation of ERK1/2 in the absence of ligand stimulation. Stimulation of SNU-16 cells with FGF7 significantly increased the phosphorylation of ERK1/2. We observed an increase in the phosphorylation of mitogen- and stress-activated kinase 2 (MSK2), p38α MAPK, 90-kD ribosomal protein kinase 1 (RSK1), Akt1, and p70S6 kinase (p70S6K). Antibody 4B9 effectively blocked the phosphorylation of all the downstream signaling proteins activated by FGF7.

Example 8

Inhibition of Tumor Xenograft Growth

To assess the activity of antibody 4B9 in vivo, we tested the effect of antibody 4B9 on the growth of human cancer xenografts harboring amplification of the FGFR2 gene. Out of the four FGFR2-amplified cell lines that were tested, only SNU-16 and MFM-223 yielded tumors in mice. Therefore, we tested the efficacy of antibody 4B9 against SNU-16 and MFM-223 xenograft tumors.

All mice were treated in accordance with the OLAW Public Health Service Policy on Human Care and Use of Laboratory Animals and the ILAR Guide for the Care and Use of Laboratory Animals. All in vivo studies were conducted following the protocols approved by the AVEO Institutional Animal Care and Use Committee. For the SNU-16 in vivo studies, 10 week old female C.B-17 SCID mice (Taconic, Germantown, N.Y.) were inoculated subcutaneously into the right flank with $5 \times 10^6$ cells in 1:1 RPMI 1640 (Invitrogen, Carlsbad, Calif.)/Matrigel (BD Biosciences, San Jose Calif.). Tumor measurements were taken twice weekly, using vernier calipers. Tumor volume was calculated using the formula: $V = 0.5 \times width \times width \times length$. When tumors approached a volume of 200 $mm^3$, mice were randomized into five groups of ten animals. The next day, mice were treated with 20 mg/kg mIgG (BioXCell; West Lebanon, N.H.), 2 mg/kg 4B9, 5 mg/kg 4B9, 10 mg/kg 4B9, or 20 mg/kg 4B9 by intraperitoneal injection. Mice were dosed twice weekly for the duration of the study. Seventy-two hours after the final dose tumor volumes were measured again for calculation of tumor growth inhibition. All statistical analysis was done using GraphPad PRISM® Version 4.00. Final tumor volumes were analyzed using with a one-way analysis of variance and Tukey multiple comparison test.

Figure 6:
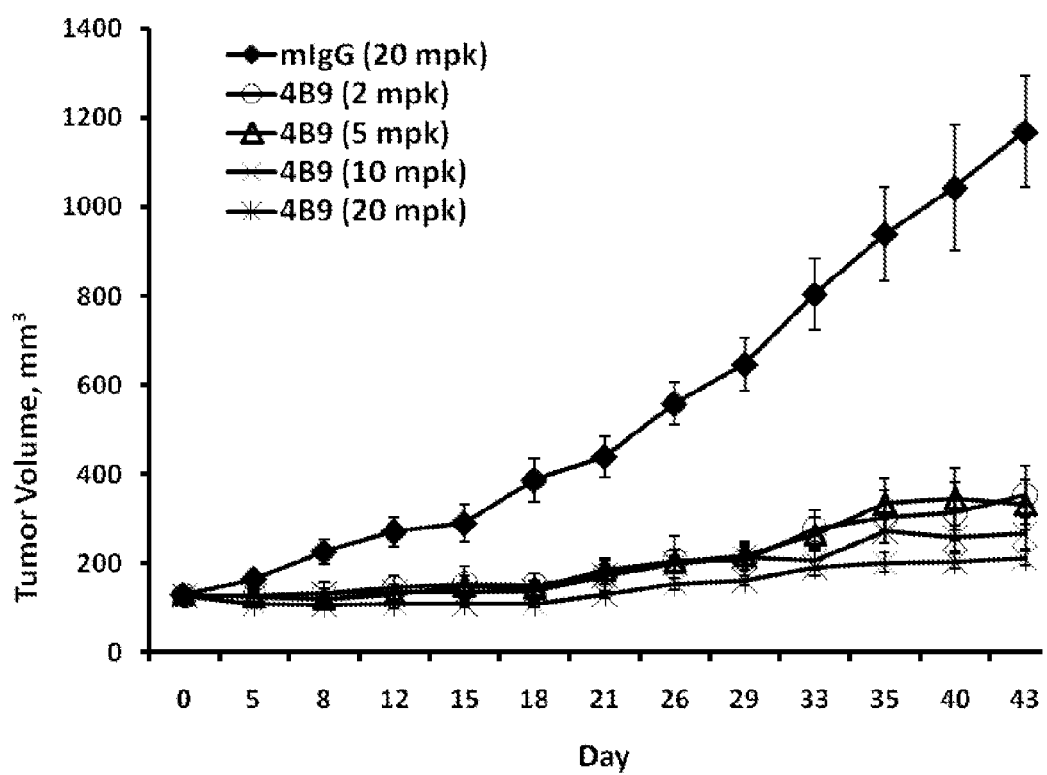
FIG. 6 is a graph summarizing results from an experiment to measure inhibition of growth of SNU-16 xenograft tumors by treatment with antibody 4B9 at 2 mg/kg (also referred to herein as "mpk") (○), 5 mpk (Δ), 10 mpk (x) or 20 mpk (*), with mIgG at 20 mpk (◆) serving as a negative control.

SNU-16 xenograft tumors were treated with a control murine IgG at 20 mg/kg or antibody 4B9 at 2, 5, 10 or 20 mg/kg. As shown in FIG. 6, each 4B9 treatment group showed significant tumor growth inhibition, as compared to mIgG treated controls (70, 72, 77, and 82%, respectively p<0.001) at day 43, which was the last day for the control group to remain in the study. All treatments were well-tolerated with no significant body weight loss. The tumor lysates were also analyzed. Concomitant with inhibition of tyrosine phosphorylation of FGFR2, antibody 4B9 downregulated the total amount of FGFR2 protein in tumors. No significant difference in the total ERK1/2 or phospho-ERK1/2 was detected in the tumors samples treated with control IgG or 4B9 from tumors collected at the end of study. In contrast to the phospho-receptor tyrosine kinase (RTK) profile of SNU-16 cells in vitro, RTK array analysis of SNU-16 xenografts revealed that FGFR2 was the predominant RTK that was tyrosine phosphorylated in vivo, and 4B9 significantly inhibited FGFR2 tyrosine phosphorylation in two of the 4B9-treated SNU-16 tumors tested. In vitro, the proliferation of SNU-16 cells was not sensitive to the treatment of 4B9. Tyrosine phosphorylation of FGFR2 in SNU-16 cells in vivo suggests that the dependence of SNU-16 xenografts on activated FGFR2 signaling in vivo explains their sensitivity to treatment with antibody 4B9.

The effect of antibody 4B9 was also investigated on the in vivo growth of FGFR2-amplified breast cancer cell line MFM-223. For these studies, 5-week old female NCr nude mice (Taconic; Germantown, N.Y.) were implanted subcutaneously on the left flank with 0.72 mg 90-day release 17-β estradiol pellets (Innovative Research; Sarasota, Fla.) and inoculated subcutaneously into the right flank with $10 \times 10^6$ MFM-223 cells in 1:1 EMEM (ATCC; Manassas, Va.)/Matrigel. When tumors approached a volume of 200 $mm^3$, mice were randomized into two groups of ten animals and treated IP with 20 mg/kg mIgG (BioXCell; West Lebanon, N.H.) or 20 mg/kg 4B9. Mice were dosed twice weekly for the duration of the study. All statistical analysis was done using GraphPad PRISM® Version 4.00. Since there were only two groups in this study final tumor volumes and weights (Day 27, 48 hours after final dose) were analyzed with an unpaired two tailed t-test.

Figure 7:
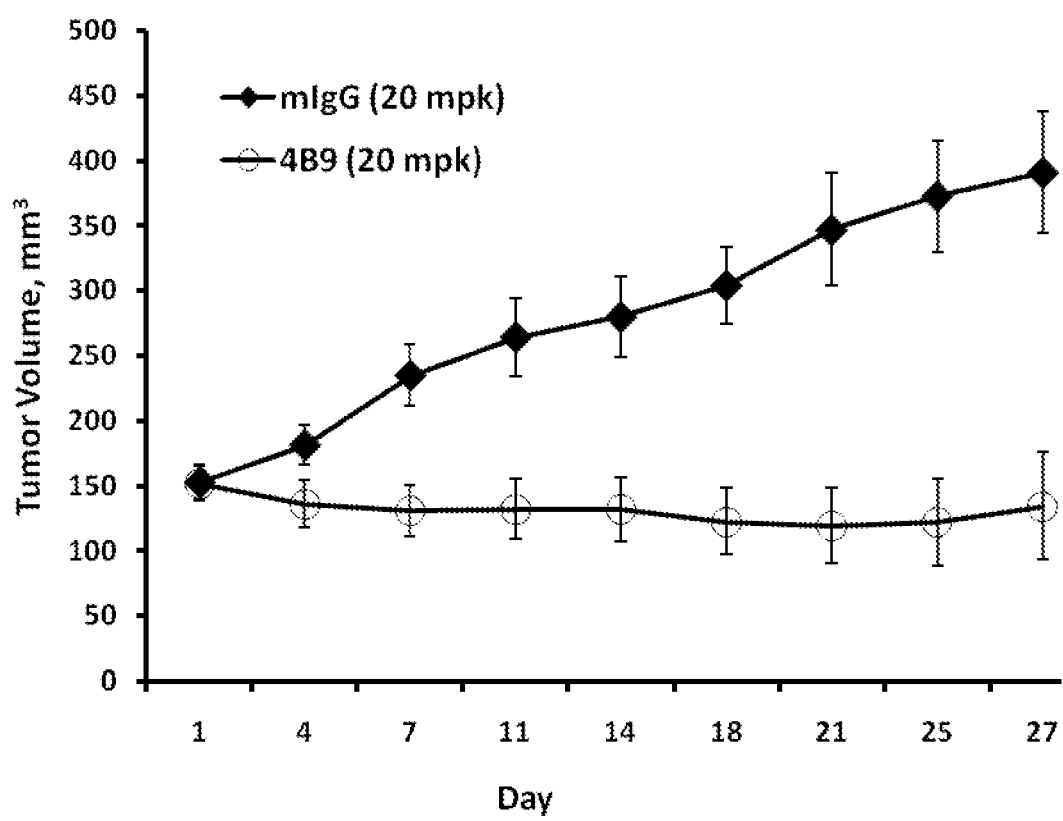
FIG. 7 is a graph summarizing results from an experiment to measure the effect of antibody 4B9 (○) on the in vivo growth of FGFR2-amplified breast cancer cell line MFM-223 (murine IgG (◆)).

On day 25, in the MFM-223 xenografts, there was greater than 66% inhibition of tumor volumes (p=0.0015; FIG. 7) and final tumor weights (p=0.0188) in 4B9 treated mice, as compared to mIgG-treated controls. All treatments were well-tolerated, with no significant body weight loss. Similar to what was observed in SNU-16 xenografts, 4B9 strongly down-regulated the total FGFR2 protein in tumors, concomitant with inhibition of tyrosine phosphorylation of FGFR2. No significant difference in the total or phosphor-ERK1/2 was detected in the tumors samples either treated with the control IgG or 4B9 from tumors collected at the end of study.

Example 9

Humanization of Anti-FGFR2 Antibodies

A. Construction of Humanized FGFR2 Antibodies

This Example describes the humanization of the murine antibody designated 4B9, and the characterization of the resulting humanized antibodies. The humanized anti-FGFR2 IIIb antibodies were designed using methods well-known in the art. The designed amino acid sequences were converted to codon-optimized DNA sequences and synthesized by DNA 2.0, Inc. to include (in the following order): 5' HindIII restriction site, Kozak consensus sequence, amino terminal signal sequence, humanized variable region, human IgG 1 or Kappa constant region, stop codon, and a 3' EcoRI restriction site.

The humanized heavy chains were subcloned into pEE6.4 (Lonza, Basel, Switzerland) via HindIII and EcoRI sites using In-Fusion™ PCR cloning (Clontech, Mountain View, Calif.). The humanized Kappa light chains were subcloned into pEE14.4 (Lonza) via HindIII and EcoRI sites using In-Fusion™ PCR cloning.

Humanized antibody chains were transiently transfected into 293T cells to produce antibody. Antibody was purified for subsequent in vitro analysis. Binding of the humanized antibodies to human FGFR2 IIIb was measured as described below. The results are summarized in Tables 12 and 13.

Each of the possible combinations of the humanized immunoglobulin heavy chain and immunoglobulin light chain variable regions are set forth below in Table 6.

TABLE 6

| Light Chain Variable Region | Heavy Chain Variable Region |
| --- | --- |
| Hu4B9-65 Kappa (SEQ ID NO: 40) | Hu4B9-65 Heavy (SEQ ID NO: 35) |
| Hu4B9-65 Kappa (SEQ ID NO: 40) | Hu4B9-82, -83 Heavy (SEQ ID NO: 37) |
| Hu4B9-82 Kappa (SEQ ID NO: 44) | Hu4B9-65 Heavy (SEQ ID NO: 35) |
| Hu4B9-82 Kappa (SEQ ID NO: 44) | Hu4B9-82, -83 Heavy (SEQ ID NO: 37) |
| Hu4B9-83 Kappa (SEQ ID NO: 46) | Hu4B9-65 Heavy (SEQ ID NO: 35) |
| Hu4B9-83 Kappa (SEQ ID NO: 46) | Hu4B9-82, -83 Heavy (SEQ ID NO: 37) |

The nucleic acid sequences encoding and the protein sequences defining variable regions of the humanized 4B9 antibodies are summarized below (amino terminal signal peptide sequences are not shown). CDR sequences (Kabat definition) are shown in bold and are underlined in the amino acid sequences.

Nucleic Acid Sequence Encoding the Hu4B9-65 Heavy Chain Variable
Region
(SEQ ID NO: 34)
```
  1 caagtgcagc tcgtccaatc gggagccgaa gtgaagaagc ctggttcctc ggtaaaagta
 61 agctgtaagg cgtccggtta cacgtttacc tcatattgga tgcactgggt cagacaggca
121 cccggacagg gactcgagtg gatgggagcg atctacccgg caattcgga cactgattac
181 agccagaaat tcaaggggag ggtcacgatc acggcagatg agcacatc aacagcctat
241 atggagctgt cgtcgcttcg gagcgaggac acggcggtct actactgctc caaattcgac
301 tattgggggc aggggacctt ggtgaccgtg tcatcc
```

Protein Sequence Defining the Hu4B9-65 Heavy Chain Variable Region
(SEQ ID NO: 35)
```
  1 qvqlvqsgae vkkpgssvkv sckasgytft sywmhwvrqa pgqglewmga iypgnsdtdy
 61 sqkfkgrvti tadeststay melsslrsed tavyycskfd ywgqgtivtv ss
```

Nucleic Acid Sequence Encoding the Hu4B9-82, -83 Heavy Chain Variable
Region
(SEQ ID NO: 36)
```
  1 caagtgcagc tcgtccaatc gggagccgaa gtgaagaagc ctggttcctc ggtaaaagta
 61 agctgtaagg cgtccggtta cacgttttcc tcatattgga tgcactgggt cagacaggca
121 cccggacagg gactcgagtg gatgggagcg atctacccgg caattcgga cactgattac
181 agccagaaat tccaggggag ggtcacgatc acggcagatg agcacatc aacagcctat
241 atggagctgt cgtcgcttcg gagcgaggac acggcggtct actactgctc caaattcgac
301 tattgggggc aggggacctt ggtgaccgtg tcatcc
```

Protein Sequence Defining the Hu4B9-82, -83 Heavy Chain Variable
Region
(SEQ ID NO: 37)
```
  1 qvqlvqsgae vkkpgssvkv sckasgytfs sywmhwvrqa pgqglewmga iypgnsdtdy
 61 sqkfqgrvti tadeststay melsslrsed tavyycskfd ywgqgtivtv ss
```

Nucleic Acid Sequence Encoding the Hu4B9-65 Kappa Chain Variable
Region
(SEQ ID NO: 39)
```
  1 gaaattgtgc tgacccagag cccggcgacc ctgagcctga gcccgggcga acgcgcgacc
 61 ctgagctgcc gcgcgagcag cagcgtgaac tatatgtatt ggtatcagca gaaaccgggc
121 caggcgccgc gcccgtggat ttatctgacc agcaaccgcg cgaccggcgt gccggcgcgc
181 tttagcggca gcggcagcgg caccgattat accctgacca ttagcagcct ggaaccggaa
241 gattttgcgg tgtattattg ccagcagtgg agcagcaacc cgtataccct tggccagggc
301 accaaactgg aaattaaa
```

Protein Sequence Defining the Hu4B9-65 Kappa Chain Variable Region
(SEQ ID NO: 40)
```
  1 eivltqspat lslspgerat lscrasssvn ymywyqqkpg qaprpwiylt snratgvpar
 61 fsgsgsgtdy tltisslepe dfavyycqqw ssnpytfgqg tkleik
```

Nucleic Acid Sequence Encoding the Hu4B9-82 Kappa Chain Variable
Region
(SEQ ID NO: 43)
```
  1 gaaatcgtac ttactcagag ccctgccaca ttgtcattgt cacccgggga acgcgccaca
 61 ctgtcgtgcc gggcttcatc gagcgtgaac tacatgtatt ggtatcaaca gaaaccaggc
121 caagcaccgc gaccttggat ctacttgacg agcaatcgag ccacgggtat ccccgcgagg
181 ttctccggtt cggggtcggg aactgattac acactgacaa tttcctcgct ggagcccgag
241 gacttcgcgg tgtactattg tcagcagtgg tcatccaacc cgtacacgtt tggacagggg
301 acgaagctcg agatcaag
```

Protein Sequence Defining the Hu4B9-82 Kappa Chain Variable Region
(SEQ ID NO: 44)
```
  1 eivltqspat lslspgerat lscrasssvn ymywyqqkpg qaprpwiylt snratgipar
 61 fsgsgsgtdy tltisslepe dfavyycqqw ssnpytfgqg tkleik
```

Nucleic Acid Sequence Encoding the Hu4B9-83 Kappa Chain Variable
Region
(SEQ ID NO: 45)
```
  1 gaaatcgtac ttactcagag ccctgccaca ttgtcattgt cacccgggga acgcgccaca
 61 ctgtcgtgcc gggcttcatc gagcgtgaac tacatgtatt ggtatcaaca gaaaccaggc
121 caagcaccgc gaccttggat ctacttgacg agcaatcgag ccacgggtat ccccgcgagg
181 ttctccggtt cggggtcggg aactgatttc acactgacaa tttcctcgct ggagcccgag
241 gacttcgcgg tgtactattg tcagcagtgg tcatccaacc cgtacacgtt tggacagggg
301 acgaagctcg agatcaag
```

Protein Sequence Defining the Hu4B9-83 Kappa Chain Variable Region
(SEQ ID NO: 46)
```
  1 eivltqspat lslspgerat lscrasssvn ymywyqqkpg qaprpwiylt snratgipar
 61 fsgsgsgtdf tltisslepe dfavyycqqw ssnpytfgqg tkleik
```

The amino acid sequences defining the immunoglobulin heavy chain variable regions for the antibodies produced in Example 9 are aligned in FIG. 8. Amino terminal signal peptide sequences (for proper expression/secretion) are not shown. CDR$_1$, CDR$_2$, and CDR$_3$ (Kabat definition) are identified by boxes (See FIG. 9).

The amino acid sequences defining the immunoglobulin light chain variable regions for the antibodies in Example 9 are aligned in FIG. 10. Amino terminal signal peptide sequences (for proper expression/secretion) are not shown. CDR$_1$, CDR$_2$ and CDR$_3$ (Kabat definition) are identified by boxes (See FIG. 11).

Table 7 is a concordance chart showing the SEQ ID NO. of each sequence discussed in this Example.

TABLE 7

| SEQ. ID NO. | Nucleic Acid or Protein |
|---|---|
| 34 | Hu4B9-65 Heavy Chain Variable Region—nucleic acid |
| 35 | Hu4B9-65 Heavy Chain Variable Region—protein |
| 5 | Hu4B9-65 Heavy Chain CDR$_1$ (Kabat definition) |
| 6 | Hu4B9-65 Heavy Chain CDR$_2$ (Kabat definition) |
| 11 | Hu4B9-65 Heavy Chain CDR$_3$ (IGMT definition) |
| 36 | Hu4B9-82, -83 Heavy Chain Variable Region—nucleic acid |
| 37 | Hu4B9-82, -83 Heavy Chain Variable Region—protein |
| 5 | Hu4B9-82, -83 Heavy Chain CDR$_1$ (Kabat definition) |
| 38 | Hu4B9-82, -83 Heavy Chain CDR$_2$ (Kabat definition) |
| 11 | Hu4B9-82, -83 Heavy Chain CDR$_3$ (IGMT definition) |
| 39 | Hu4B9-65 Light (kappa) Chain Variable Region—nucleic acid |
| 40 | Hu4B9-65 Light (kappa) Chain Variable Region—protein |
| 41 | Hu4B9-65 Light (kappa) Chain CDR$_1$ (Kabat definition) |
| 42 | Hu4B9-65 Light (kappa) Chain CDR$_2$ (Kabat definition) |
| 14 | Hu4B9-65 Light (kappa) Chain CDR$_3$ (Kabat definition) |
| 43 | Hu4B9-82 Light (kappa) Chain Variable Region—nucleic acid |
| 44 | Hu4B9-82 Light (kappa) Chain Variable Region—protein |
| 41 | Hu4B9-82 Light (kappa) Chain CDR$_1$ (Kabat definition) |
| 42 | Hu4B9-82 Light (kappa) Chain CDR$_2$ (Kabat definition) |
| 14 | Hu4B9-82 Light (kappa) Chain CDR$_3$ (Kabat definition) |
| 45 | Hu4B9-83 Light (kappa) Chain Variable Region—nucleic acid |
| 46 | Hu4B9-83 Light (kappa) Chain Variable Region—protein |
| 41 | Hu4B9-83 Light (kappa) Chain CDR$_1$ (Kabat definition) |
| 42 | Hu4B9-83 Light (kappa) Chain CDR$_2$ (Kabat definition) |
| 14 | Hu4B9-83 Light (kappa) Chain CDR$_3$ (Kabat definition) |

Murine and humanized monoclonal antibody heavy chain CDR sequences (Kabat, Chothia, and IMGT definitions) are shown in Table 8.

TABLE 8

| | CDR1 | CDR2 | CDR3 |
|---|---|---|---|
| | Kabat | | |
| 4B9 | SYWMH (SEQ ID NO: 5) | AIYPGNSDTDYSQK FKG (SEQ ID NO: 6) | FDY |
| Hu4B9-65 | SYWMH (SEQ ID NO: 5) | AIYPGNSDTDYSQK FKG (SEQ ID NO: 6) | FDY |
| Hu4B9-82, -83 | SYWMH (SEQ ID NO: 5) | AIYPGNSDTDYSQK FQG (SEQ ID NO: 38) | FDY |
| | CHOTHIA | | |
| 4B9 | GYTFTSY (SEQ ID NO: 7) | YPGNSD (SEQ ID NO: 8) | FDY |
| Hu4B9-65 | GYTFTSY (SEQ ID NO: 7) | YPGNSD (SEQ ID NO: 8) | FDY |
| Hu4B9-82, -83 | GYTFSSY (SEQ ID NO: 47) | YPGNSD (SEQ ID NO: 8) | FDY |
| | IMGT | | |
| 4B9 | GYTFTSYW (SEQ ID NO: 9) | IYPGNSDT (SEQ ID NO: 10) | SKFDY (SEQ ID NO: 11) |
| Hu4B9-65 | GYTFTSYW (SEQ ID NO: 9) | IYPGNSDT (SEQ ID NO: 10) | SKFDY (SEQ ID NO: 11) |
| Hu4B9-82, -83 | GYTFSSYW (SEQ ID NO: 48) | IYPGNSDT (SEQ ID NO: 10) | SKFDY (SEQ ID NO: 11) |

Murine and humanized monoclonal antibody Kappa light chain CDR sequences (Kabat, Chothia, and IMGT definitions) are shown in Table 9.

TABLE 9

| | CDR1 | CDR2 | CDR3 |
|---|---|---|---|
| | Kabat/Chothia | | |
| 4B9 | SASSSVNYMY (SEQ ID NO: 12) | LTSNLAS (SEQ ID NO: 13) | QQWSSNPYT (SEQ ID NO: 14) |
| Hu4B9-65 | RASSSVNYMY (SEQ ID NO: 41) | LTSNRAT (SEQ ID NO: 42) | QQWSSNPYT (SEQ ID NO: 14) |
| Hu4B9-82 | RASSSVNYMY (SEQ ID NO: 41) | LTSNRAT (SEQ ID NO: 42) | QQWSSNPYT (SEQ ID NO: 14) |
| Hu4B9-83 | RASSSVNYMY (SEQ ID NO: 41) | LTSNRAT (SEQ ID NO: 42) | QQWSSNPYT (SEQ ID NO: 14) |
| | IGMT | | |
| 4B9 | SSVNY (SEQ ID NO: 15) | LTS | QQWSSNPYT (SEQ ID NO: 14) |
| Hu4B9-65 | SSVNY (SEQ ID NO: 15) | LTS | QQWSSNPYT (SEQ ID NO: 14) |
| Hu4B9-82 | SSVNY (SEQ ID NO: 15) | LTS | QQWSSNPYT (SEQ ID NO: 14) |
| Hu4B9-83 | SSVNY (SEQ ID NO: 15) | LTS | QQWSSNPYT (SEQ ID NO: 14) |

To create the complete humanized heavy or kappa chain antibody sequences, each variable sequence above is combined with its respective human constant region. For example, a complete heavy chain comprises a heavy variable sequence followed by a human IgG1 heavy chain constant sequence. A complete kappa chain comprises a kappa variable sequence followed by the human kappa light chain constant sequence.

Nucleic Acid Sequence Encoding the Human IgG1 Heavy Chain Constant
Region (SEQ ID NO: 49)

```
  1 gcctcaacaa aaggaccaag tgtgttccca ctcgcccta gcagcaagag tacatccggg
 61 ggcactgcag cactcggctg cctcgtcaag gattattttc cagagccagt aaccgtgagc
121 tggaacagtg gagcactcac ttctggtgtc catactttc ctgctgtcct gcaaagctct
181 ggcctgtact cactcagctc cgtcgtgacc gtgccatctt catctctggg cactcagacc
241 tacatctgta atgtaaacca caagcctagc aatactaagg tcgataagcg ggtgaaccc
301 aagagctgcg acaagactca cacttgtccc ccatgccctg ccctgaact tctgggcggt
361 cccagcgtct ttttgttccc accaaagcct aaagatactc tgatgataag tagaacaccc
421 gaggtgacat gtgttgttgt agacgtttcc cacgaggacc cagaggttaa gttcaactgg
481 tacgttgatg gagtcgaagt acataatgct aagaccaagc ctagagagga gcagtataat
541 agtacatacc gtgtagtcag tgttctcaca gtgctgcacc aagactggct caacggcaaa
601 gaatacaaat gcaaagtgtc caacaaagca ctcccagccc ctatcgagaa gactattagt
661 aaggcaaagg ggcagcctcg tgaaccacag gtgtacactc tgccacccag tagagaggaa
721 atgacaaaga accaagtctc attgacctgc ctggtgaaag gcttctaccc cagcgacatc
781 gccgttgagt gggagagtaa cggtcagcct gagaacaatt acaagacaac ccccccagtg
841 ctggatagtg acgggtcttt ctttctgtac agtaagctga ctgtggacaa gtcccgctgg
901 cagcagggta acgtcttcag ctgttccgtg atgcacgagg cattgcacaa ccactacacc
961 cagaagtcac tgagcctgag cccagggaag
```

Protein Sequence Defining the Human IgG1 Heavy Chain Constant
Region (SEQ ID NO: 50)

```
  1 astkgpsvfp lapsskstsg gtaalgclvk dyfpepvtvs wnsgaltsgv htfpavlqss
 61 glyslssvvt vpssslgtqt yicnvnhkps ntkvdkrvep kscdkthtcp pcpapellgg
121 psvflfppkp kdtlmisrtp evtcvvvdvs hedpevkfnw yvdgvevhna ktkpreeqyn
181 styrvvsvlt vlhqdwlngk eykckvsnka lpapiektis kakgqprepq vytlppsree
241 mtknqvsltc lvkgfypsdi avewesngqp ennykttppv ldsdgsffly skltvdksrw
301 qqgnvfscsv mhealhnhyt qkslslspgk
```

Nucleic Acid Sequence Encoding the Human Kappa Light Chain Constant
Region (SEQ ID NO: 51)

```
  1 cgcacagttg ctgcccccag cgtgttcatt ttcccaccta gcgatgagca gctgaaaagc
 61 ggtactgcct ctgtcgtatg cttgctcaac aacttttacc cacgtgaggc taaggtgcag
121 tggaaagtgg ataatgcact tcaatctgga aacagtcaag agtccgtgac agaacaggac
181 agcaaagact caacttattc actctcttcc accctgactc tgtccaaggc agactatgaa
241 aaacacaagg tatacgcctg cgaggttaca caccagggtt tgtctagtcc tgtcaccaag
301 tccttcaata ggggcgaatg t
```

Protein Sequence Defining the Human Kappa Light Chain Constant Region (SEQ ID NO: 52)

```
  1 rtvaapsvfi fppsdeqlks gtasvvclln nfypreakvq wkvdnalqsg nsqesvteqd
 61 skdstyslss tltlskadye khkvyacevt hqglsspvtk sfnrgec
```

The following sequences represent the actual or contemplated full length heavy and light chain sequences (i.e., containing both the variable and constant regions sequences) for each antibody described in this Example. Signal sequences for proper secretion of the antibodies are also included at the 5' end of the DNA sequences or the amino terminal end of the protein sequences. It is also contemplated herein that the variable region sequences can be ligated to other constant region sequences to produce active full length IgG heavy and light chains.

Nucleic Acid Sequence Encoding the Full Length Humanized Hu4B9-65
Heavy Chain (Humanized Heavy Chain Variable Region and Human IgG1
Constant Region)

(SEQ ID NO: 53)

```
   1 atggacatga gagttcctgc tcagctgctc gggttgctgt tgctttggct ccggggtgct
  61 aggtgccaag tgcagctcgt ccaatcggga gccgaagtga agaagcctgg ttcctcggta
 121 aaagtaagct gtaaggcgtc cggttacacg tttacctcat attggatgca ctgggtcaga
 181 caggcacccg gacagggact cgagtggatg ggagcgatct acccgggcaa ttcggacact
 241 gattacagcc agaaattcaa ggggagggtc acgatcacgg cagatgagag cacatcaaca
 301 gcctatatgg agctgtcgtc gcttcggagc gaggacacgg cggtctacta ctgctccaaa
 361 ttcgactatt ggggcaggg gaccttggtg accgtgtcat ccgcctcaac aaaaggacca
 421 agtgtgttcc cactcgcccc tagcagcaag agtacatccg gggcactgc agcactcggc
 481 tgcctcgtca aggattattt tccagagcca gtaaccgtga gctggaacag tggagcactc
 541 actttctggtg tccatacttt tcctgctgtc ctgcaaagct ctggcctgta ctcactcagc
 601 tccgtcgtga ccgtgccatc ttcatctctg ggcactcaga cctacatctg taatgtaaac
 661 cacaagccta gcaatactaa ggtcgataag cgggtggaac ccaagagctg cgacaagact
 721 cacacttgtc cccatgccc tgcccctgaa cttctgggcg gtcccagcgt ctttttgttc
 781 ccaccaaagc ctaaagatac tctgatgata agtagaacac ccgaggtgac atgtgttgtt
 841 gtagacgttt cccacgagga cccagaggtt aagttcaact ggtacgttga tggagtcgaa
 901 gtacataatg ctaagaccaa gcctagagag gagcagtata atagtacata ccgtgtagtc
 961 agtgttctca gtgctgca ccaagactgg ctcaacggca agaatacaa atgcaaagtg
1021 tccaacaaag cactcccagc cctatcgag aagactatta gtaaggcaaa ggggcagcct
1081 cgtgaaccac aggtgtacac tctgccaccc agtagagagg aaatgacaaa gaaccaagtc
1141 tcattgacct gcctggtgaa aggcttctac cccagcgaca tcgccgttga gtgggagagt
```

```
1201 aacggtcagc ctgagaacaa ttacaagaca accccccag tgctggatag tgacgggtct
1261 ttctttctgt acagtaagct gactgtggac aagtcccgct ggcagcaggg taacgtcttc
1321 agctgttccg tgatgcacga ggcattgcac aaccactaca cccagaagtc actgagcctg
1381 agcccaggga ag
```

Protein Sequence Defining the Full Length Humanized Hu4B9-65 Heavy Chain (Humanized Heavy Chain Variable Region and Human IgG1 Constant Region)

(SEQ ID NO: 54)
```
  1 mdmrvpaqll glllllwrga rcqvqlvqsg aevkkpgssv kvsckasgyt ftsywmhwvr
 61 qapgqglewm gaiypgnsdt dysqkfkgry titadestst aymelsslrs edtavyycsk
121 fdywgqgtiv tvssastkgp svfplapssk stsggtaalg clvkdyfpep vtvswnsgal
181 tsgvhtfpav lqssglysls svvtvpsssl gtqtyicnvn hkpsntkvdk rvepkscdkt
241 htcppcpape llggpsvflf ppkpkdtlmi srtpevtcvv vdvshedpev kfnwyvdgve
301 vhnaktkpre eqynstyrvv svltvlhqdw lngkeykckv snkalpapie ktiskakgqp
361 repqvytlpp sreemtknqv sltclvkgfy psdiavewes ngqpennykt tppvldsdgs
421 fflysklrvd ksrwqqgnvf scsvmhealh nhytqkslsl spgk
```

Nucleic Acid Sequence Encoding the Full Length Humanized Hu4B9-82, -83 Heavy Chain (Humanized Heavy Chain Variable Region and Human IgG1 Constant Region)

(SEQ ID NO: 55)
```
   1 atggacatga gagttcctgc tcagctgctc gggttgctgt tgctttggct ccggggtgct
  61 aggtgccaag tgcagctcgt ccaatcggga gccgaagtga agaagcctgg ttcctcggta
 121 aaagtaagct gtaaggcgtc cggttacacg ttttcctagc attggatgca ctgggtcaga
 181 caggcacccg gacagggact cgagtggatg ggagcgatct acccgggcaa ttcggacact
 241 gattacagcc agaaattcca ggggagggtc acgatcacgg cagatgagag cacatcaaca
 301 gcctatatgg agctgtcgtc gcttcggagc gaggacacgg cggtctacta ctgctccaaa
 361 ttcgactatt ggggcaggg gaccttggtg accgtgtcat ccgcctcaac aaaaggacca
 421 agtgtgttcc cactcgcccc tagcagcaag agtacatccg ggggcactgc agcactcggc
 481 tgcctcgtca aggattattt tccagagcca gtaaccgtga gctggaacag tggagcactc
 541 acttctggtg tccatacttt tcctgctgtc ctgcaaagct ctggcctgta ctcactcagc
 601 tccgtcgtga ccgtgccatc ttcatctctg ggcactcaga cctacatctg taatgtaaac
 661 cacaagccta gcaatactaa ggtcgataag cgggtggaac ccaagagctg cgacaagact
 721 cacacttgtc cccatgcc tgccctgaa cttctgggcg gtcccagcgt cttttgttc
 781 ccaccaaagc ctaaagatac tctgatgata agtagaaccc ccgaggtgac atgtgttgtt
 841 gtagacgttt ccacgagga cccagaggtt aagttcaact ggtacgttga tggagtcgaa
 901 gtacataatg ctaagaccaa gcctagagag gagcagtata atagtacata ccgtgtagtc
 961 agtgttctca cagtgctgca ccaagactgg ctcaacggca agaatacaa atgcaaagtg
1021 tccaacaaag cactcccagc ccctatcgag aagactatta gtaaggcaaa ggggcagcct
1081 cgtgaaccac aggtgtacac tctgccaccc agtagagagg aaatgacaaa gaaccaagtc
1141 tcattgacct gcctggtgaa aggcttctac cccagcgaca tcgccgttga gtgggagagt
1201 aacggtcagc ctgagaacaa ttacaagaca accccccag tgctggatag tgacgggtct
1261 ttctttctgt acagtaagct gactgtggac aagtcccgct ggcagcaggg taacgtcttc
1321 agctgttccg tgatgcacga ggcattgcac aaccactaca cccagaagtc actgagcctg
1381 agcccaggga ag
```

Protein Sequence Defining the Full Length Humanized Hu4B9-82, -83 Heavy Chain (Humanized Heavy Chain Variable Region and Human IgG1 Constant Region)

(SEQ ID NO: 56)
```
  1 mdmrvpaqll glllllwrga rcqvqlvqsg aevkkpgssv kvsckasgyt fssywmhwvr
 61 qapgqglewm gaiypgnsdt dysqkfkgrv titadestst aymelsslrs edtavyycsk
121 fdywgqgtlv tvssastkgp svfplapssk stsggtaalg clvkdyfpep vtvswnsgal
181 tsgvhtfpav lqssglysls svvtvpsssl gtqtyicnvn hkpsntkvdk rvepkscdkt
241 htcppcpape llggpsvflf ppkpkdtlmi srtpevtcvv vdvshedpev kfnwyvdgve
301 vhnaktkpre eqynstyrvv svltvlhqdw lngkeykckv snkalpapie ktiskakgqp
361 repqvytlpp sreemtknqv sltclvkgfy psdiavewes ngqpennykt tppvldsdgs
421 fflysklrvd ksrwqqgnvf scsvmhealh nhytqkslsl spgk
```

Nucleic Acid Sequence Encoding the Full Length Humanized Hu4B9-65 Light Chain (Humanized Kappa Chain Variable Region and Human Constant Region)

(SEQ ID NO: 57)
```
  1 atggacatga gggtgcccgc tcaactgctg ggctgctgc tgctgtggct gagaggagct
 61 cgttgcgaaa ttgtgctgac ccagagcccg cgaccctga gcctgagccc gggcgaacgc
121 gcgaccctga gctgccgcgc gagcagcagc gtgaactata tgtattggta tcagcagaaa
181 ccgggccagg cgccgcgccc gtggatttat ctgaccagca accgcgcgac cggcgtgccg
241 gcgcgcttta gcggcagcgg cagcggcacc gattataccc tgaccattag cagcctggaa
301 ccggaagatt ttgcggtgta ttattgccag cagtgggca gcaaccgta ccctttggc
361 cagggcacca aactggaaat taacgcaca gttgctgccc cagcgtgtt catttccca
421 cctagcgatg agcagctgaa aagcggtact gcctctgtcc tatgcttgct caacaactt
481 tacccacgtg aggctaaggt gcagtggaaa gtggataatg cacttcaatc tggaaacagt
541 caagagtccg tgacagaaca ggacagcaaa gactcaactt attcactctc ttccaccctg
601 actctgtcca aggcagacta tgaaaaacac aaggtatacg cctgcgaggt tacacaccag
661 ggtttgtcta gtcctgtcac caagtccttc aatagggggcg aatgt
```

-continued

Protein Sequence Defining the Full Length Humanized Hu4B9-65 Light
Chain (Humanized Kappa Chain Variable Region and Human Constant
Region)
(SEQ ID NO: 58)
```
  1 mdmrvpaqll gllllwlrga rceivltqsp atlslspger atlscrasss vnymywyqqk
 61 pgqaprpwiy ltsnratgvp arfsgsgsgt dytltissle pedfavyycq qwssnpytfg
121 qgtkleikrt vaapsvfifp psdeqlksgt asvvcllnnf ypreakvqwk vdnalqsgns
181 qesvteqdsk dstyslsstl tlskadyekh kvyacevthq glsspvtksf nrgec
```

Nucleic Acid Sequence Encoding the Full Length Humanized Hu4B9-82
Light Chain (Humanized Kappa Chain Variable Region and Human Constant
Region)
(SEQ ID NO: 59)
```
  1 atggacatga gggtgcccgc tcaactgctg gggctgctgc tgctgtggct gagaggagct
 61 cgttgcgaaa tcgtacttac tcagagccct gccacattgt cattgtcacc cggggaacgc
121 gccacactgt cgtgccgggc ttcatcgagc gtgaactaca tgtattggta tcaacagaaa
181 ccaggccaag caccgcgacc ttggatctac ttgacgagca atcgagccac gggtatcccc
241 gcgaggttct ccggttcggg gtcgggaact gattacacac tgacaatttc ctcgctggag
301 cccgaggact tcgcggtgta ctattgtcag cagtggtcat ccaacccgta cacgtttgga
361 caggggacga agctcgagat caagcgcaca gttgctgccc ccagcgtgtt cattttccca
421 cctagcgatg agcagctgaa aagcggtact gcctctgtcg tatgcttgct caacaacttt
481 tacccacgtg aggctaaggt gcagtggaaa gtggataatg cacttcaatc tggaaacagt
541 caagagtccg tgacagaaca ggacagcaaa gactcaactt attcactctc ttccaccctg
601 actctgtcca aggcagacta tgaaaaacac aaggtatacg cctgcgaggt tacacaccag
661 ggtttgtcta gtcctgtcac caagtccttc aatagggggcg aatgt
```

Protein Sequence Defining the Full Length Humanized Hu4B9-82 Light
Chain (Humanized Kappa Chain Variable Region and Human Constant
Region)
(SEQ ID NO: 60)
```
  1 mdmrvpaqll gllllwlrga rceivltqsp atlslspger atlscrasss vnymywyqqk
 61 pgqaprpwiy ltsnratgip arfsgsgsgt dytltissle pedfavyycq qwssnpytfg
121 qgtkleikrt vaapsvfifp psdeqlksgt asvvcllnnf ypreakvqwk vdnalqsgns
181 qesvteqdsk dstyslsstl tlskadyekh kvyacevthq glsspvtksf nrgec
```

Nucleic Acid Sequence Encoding the Full Length Humanized Hu4B9-83
Light Chain (Humanized Kappa Chain Variable Region and Human Constant
Region)
(SEQ ID NO: 61)
```
  1 atggacatga gggtgcccgc tcaactgctg gggctgctgc tgctgtggct gagaggagct
 61 cgttgcgaaa tcgtacttac tcagagccct gccacattgt cattgtcacc cggggaacgc
121 gccacactgt cgtgccgggc ttcatcgagc gtgaactaca tgtattggta tcaacagaaa
181 ccaggccaag caccgcgacc ttggatctac ttgacgagca atcgagccac gggtatcccc
241 gcgaggttct ccggttcggg gtcgggaact gatttcacac tgacaatttc ctcgctggag
301 cccgaggact tcgcggtgta ctattgtcag cagtggtcat ccaacccgta cacgtttgga
361 caggggacga agctcgagat caagcgcaca gttgctgccc ccagcgtgtt cattttccca
421 cctagcgatg agcagctgaa aagcggtact gcctctgtcg tatgcttgct caacaacttt
481 tacccacgtg aggctaaggt gcagtggaaa gtggataatg cacttcaatc tggaaacagt
541 caagagtccg tgacagaaca ggacagcaaa gactcaactt attcactctc ttccaccctg
601 actctgtcca aggcagacta tgaaaaacac aaggtatacg cctgcgaggt tacacaccag
661 ggtttgtcta gtcctgtcac caagtccttc aatagggggcg aatgt
```

Protein Sequence Defining the Full Length Humanized Hu4B9-83 Light
Chain (Humanized Kappa Chain Variable Region and Human Constant
Region)
(SEQ ID NO: 62)
```
  1 mdmrvpaqll gllllwlrga rceivltqsp atlslspger atlscrasss vnymywyqqk
 61 pgqaprpwiy ltsnratgip arfsgsgsgt dftltissle pedfavyycq qwssnpytfg
121 qgtkleikrt vaapsvfifp psdeqlksgt asvvcllnnf ypreakvqwk vdnalqsgns
181 qesvteqdsk dstyslsstl tlskadyekh kvyacevthq glsspvtksf nrgec
```

For convenience, Table 10 provides a concordance chart showing the SEQ ID NO. of each sequence discussed in this Example.

TABLE 10

| SEQ ID NO. | Nucleic Acid or Protein |
|---|---|
| 49 | Human IgG1 constant—nucleic acid |
| 50 | Human IgG1 constant—protein |
| 51 | Human Kappa constant—nucleic acid |
| 52 | Human Kappa constant—protein |
| 53 | Humanized Hu4B9-65 Heavy Human Variable + Human IgG1 constant—nucleic acid |
| 54 | Humanized Hu4B9-65 Heavy Human Variable + Human IgG1 constant—protein |

TABLE 10-continued

| SEQ ID NO. | Nucleic Acid or Protein |
|---|---|
| 55 | Humanized Hu4B9-82, -83 Heavy Human Variable + Human IgG1 constant—nucleic acid |
| 56 | Humanized Hu4B9-82,-83 Heavy Human Variable + Human IgG1 constant—protein |
| 57 | Humanized Hu4B9-65 Human Variable + Human Kappa constant—nucleic acid |
| 58 | Humanized Hu4B9-65 Human Variable + Human Kappa constant—protein |
| 59 | Humanized Hu4B9-82 Human Variable + Human Kappa constant—nucleic acid |
| 60 | Humanized Hu4B9-82 Human Variable + Human Kappa constant—protein |

TABLE 10-continued

| SEQ ID NO. | Nucleic Acid or Protein |
|---|---|
| 61 | Humanized Hu4B9-83 Human Variable + Human Kappa constant—nucleic acid |
| 62 | Humanized Hu4B9-83 Human Variable + Human Kappa constant—protein |

Table 11 below shows antibodies containing each of the possible combinations of the full-length humanized immunoglobulin heavy and light chains.

TABLE 11

| Antibody Name | Light Chain | Heavy Chain |
|---|---|---|
| Hu4B9-65 | Hu4B9-65 Kappa (SEQ ID NO: 58) | Hu4B9-65 Heavy (SEQ ID NO: 54) |
| Hu4B9-84 | Hu4B9-65 Kappa (SEQ ID NO: 58) | Hu4B9-82, -83 Heavy (SEQ ID NO: 56) |
| Hu4B9-85 | Hu4B9-82 Kappa (SEQ ID NO: 60) | Hu4B9-65 Heavy (SEQ ID NO: 54) |
| Hu4B9-82 | Hu4B9-82 Kappa (SEQ ID NO: 60) | Hu4B9-82, -83 Heavy (SEQ ID NO: 56) |
| Hu4B9-86 | Hu4B9-83 Kappa (SEQ ID NO: 62) | Hu4B9-65 Heavy (SEQ ID NO: 54) |
| Hu4B9-83 | Hu4B9-83 Kappa (SEQ ID NO: 62) | Hu4B9-82, -83 Heavy (SEQ ID NO: 56) |

Three of the possible antibody constructs containing the full length immunoglobulin heavy and light chains containing humanized variable regions are designated below:

Hu4B9-65=Humanized Hu4B9-65 Heavy Chain Variable Region and Human IgG1 Constant Region (SEQ ID NO: 54) plus Hu4B9-65 Light Chain Variable Region and Human Kappa Constant Region (SEQ ID NO: 58)

Hu4B9-82=Humanized Hu4B9-82, -83 Heavy Chain Variable Region and Human IgG1 Constant Region (SEQ ID NO: 56) plus Hu4B9-82 Light Chain Variable Region and Human Kappa Constant Region (SEQ ID NO: 60)

Hu4B9-83=Humanized Hu4B9-82, -83 Heavy Chain Variable Region and Human IgG1 Constant Region (SEQ ID NO: 56) plus Hu4B9-83 Light Chain Variable Region and Human Kappa Constant Region (SEQ ID NO: 62)

B. Binding Affinities of Humanized Anti-FGFR2 Monoclonal Antibodies

The binding affinities and kinetics of interaction of monoclonal antibodies produced in Example 9 against monomeric recombinant human FGFR2 beta IIIb (rhFGFR2β-IIIb-cleaved) were measured by surface plasmon resonance using a Biacore T100 (Biacore (GE Healthcare), Piscataway, N.J.) instrument.

Goat anti-human IgG Fc (Jackson ImmunoResearch, Catalog No. 109-005-098) was immobilized on carboxymethylated dextran CM4 sensor chips (Biacore) by amine coupling (Biacore) using a standard coupling protocol according to the vendor's instructions. The analyses were performed at 25° C. and 37° C. using PBS (Invitrogen) containing 0.05% surfactant P20 (Biacore) as running buffer.

Purified antibodies were captured in individual flow cells at a flow rate of 10 μl/minute. Injection time was varied for each antibody to yield an $R_{max}$ between 30 and 90 RU. Buffer or rhFGFR2β-IIIb-cleaved diluted in running buffer was injected sequentially over a reference surface (no antibody captured) and the active surface (antibody to be tested) for 240 seconds at 60 μl/minute. The dissociation phase was monitored for up to 900 seconds. The surface was then regenerated with two 60 second injections of glycine pH 2.25 (made from glycine pH 2.0 (Biacore) and pH 2.5 (Biacore)) at 30 μl/minute. Experiments were conducted using concentrations of rhFGFR2β-IIIb-cleaved between 20 and 1.25 nM (a two-fold serial dilution).

Kinetic parameters were determined using the kinetic function of the BIAevaluation software (Biacore) with double reference subtraction. Kinetic parameters for each antibody, $k_a$ (association rate constant), $k_d$ (dissociation rate constant) and $K_D$ (equilibrium dissociation constant) were determined. The kinetic values of certain purified monoclonal antibodies (i.e., Hu4B9-65, Hu4B9-82, and Hu4B9-83) on rhFGFR2β-IIIb-cleaved at 25° C. are summarized in Table 12.

TABLE 12

| Antibody | ka (1/Ms) | kd (1/s) | KD (M) | n |
|---|---|---|---|---|
| hu4B9-65 | 2.4E+05 | 6.5E−05 | 2.6E−10 | 4 |
| hu4B9-82 | 1.9E+05 | 9.4E−05 | 4.9E−10 | 2 |
| hu4B9-83 | 2.6E+05 | 8.9E−05 | 3.5E−10 | 3 |

The results in Table 12 demonstrate the purified antibodies have affinities ranging from about 260 pM to about 490 pM when tested at 25° C.

The kinetic values of certain purified monoclonal antibodies (i.e., Hu4B9-65, Hu4B9-82, and Hu4B9-83) on rhFGFR2β-IIIb-cleaved at 37° C. are summarized in Table 13.

TABLE 13

| Antibody | ka (1/Ms) | kd (1/s) | KD (M) | n |
|---|---|---|---|---|
| hu4B9-65 | 3.7E+05 | 2.8E−04 | 8.9E−10 | 7 |
| hu4B9-82 | 4.0E+05 | 3.6E−04 | 9.3E−10 | 3 |
| hu4B9-83 | 3.2E+05 | 2.9E−04 | 9.2E−10 | 3 |

The results in Table 13 demonstrate the purified antibodies have affinities ranging from about 890 pM to about 930 pM when tested at 37° C.

Example 10

Anti-Proliferative Activity of Humanized Anti-FGFR2 Monoclonal Antibodies

The potency of humanized anti-FGFR2 antibodies was assessed in a cell-based proliferation assay. FDCP-1 cells expressing FGFR2-IIIb were seeded in a 96-well plate in IL-3 free medium containing 8 ng/ml of FGF1 and 5 μg/ml of heparin. Serial dilutions of the antibodies were prepared and added to the plate. After two days of incubation, cell proliferation was examined by a MTT assay as described above in Example 1.

Figure 12:
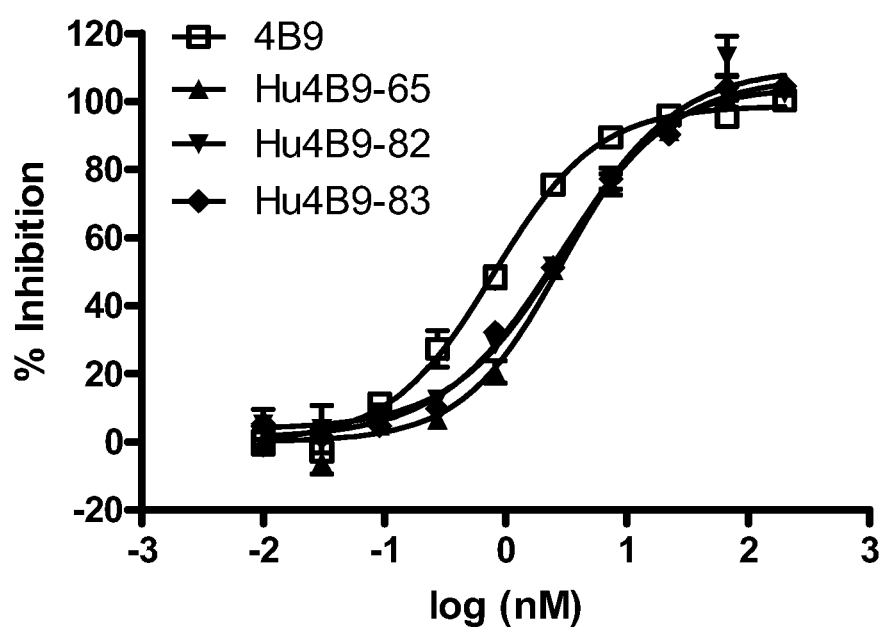
FIG. 12 is a graph summarizing results from an experiment to measure inhibition of proliferation of FDCP-1 cells expressing wild type FGFR2-IIIb by treatment with antibody 4B9 (□), Hu4B9-65 (▲), Hu4B9-82 (▼) and Hu4B9-83 (◆).

As shown in FIG. 12, humanized antibodies (Hu4B9-65, Hu4B9-82, and Hu4B9-83) demonstrated dose-dependent inhibition of FGF1-induced FDCP-FGFR2-IIIb cell proliferation. The average IC50s of the 4B9, Hu4B9-65, Hu4B9-82 and Hu4B9-83 from three independent experiments are 1.4, 4.9, 5.7 and 4.7 nM, respectively.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

What is claimed is:

1. An isolated antibody that binds human FGFR2 comprising:
   (i) an immunoglobulin heavy chain variable region comprising a $CDR_{H1}$ comprising an amino acid sequence selected from the group consisting of SEQ ID NO: 5 and SEQ ID NO: 47, a $CDR_{H2}$ comprising the amino acid sequence of SEQ ID NO: 38, and a $CDR_{H3}$ comprising the amino acid sequence of SEQ ID NO: 11; and
   (ii) an immunoglobulin light chain variable region comprising a $CDR_{L1}$ comprising the amino acid sequence of SEQ ID NO: 41, a $CDR_{L2}$ comprising the amino acid sequence of SEQ ID NO: 42, and a $CDR_{L3}$ comprising the amino acid sequence of SEQ ID NO: 14.

2. The antibody of claim 1, wherein the CDR sequences are interposed between human and humanized framework sequences.

3. An isolated antibody that binds human FGFR2 comprising an immunoglobulin heavy chain variable region comprising the amino acid sequence of SEQ ID NO: 37, and an immunoglobulin light chain variable region comprising the amino acid sequence of SEQ ID NO: 46.

4. An isolated antibody that binds human FGFR2 comprising an immunoglobulin heavy chain comprising the amino acid sequence of SEQ ID NO: 56, and an immunoglobulin light chain comprising the amino acid sequence of SEQ ID NO: 62.

5. The antibody of claim 1, wherein the antibody has a $K_D$ of 500 pM or lower as measured by surface plasmon resonance.

6. The antibody of claim 1, wherein the immunoglobulin heavy chain variable region comprises a $CDR_{H1}$ comprising the amino acid sequence of SEQ ID NO: 5, a $CDR_{H2}$ comprising the amino acid sequence of SEQ ID NO: 38, and a $CDR_{H3}$ comprising the amino acid sequence of SEQ ID NO: 11.

7. The antibody of claim 1, wherein the immunoglobulin heavy chain variable region comprises a $CDR_{H1}$ comprising the amino acid sequence of SEQ ID NO: 47, a $CDR_{H2}$ comprising the amino acid sequence of SEQ ID NO: 38, and a $CDR_{H3}$ comprising the amino acid sequence of SEQ ID NO: 11.

* * * * *